United States Patent [19]
Giordano et al.

[11] Patent Number: 6,004,749
[45] Date of Patent: *Dec. 21, 1999

[54] METHOD FOR IDENTIFYING COMPOUNDS AFFECTING RNA/RNA BINDING PROTEIN INTERACTIONS

[75] Inventors: Tony Giordano, Phoenixville, Pa.; Deborah L. Beach, Wilmington, Del.

[73] Assignee: Message Pharmaceuticals, Malvern, Pa.

[ * ] Notice: This patent is subject to a terminal disclaimer.

[21] Appl. No.: 08/903,910

[22] Filed: Jul. 31, 1997

Related U.S. Application Data

[63] Continuation-in-part of application No. 08/690,010, Jul. 31, 1996.

[51] Int. Cl.⁶ .............................. C12Q 1/68; C07K 14/00; C07H 21/02; G01N 33/566
[52] U.S. Cl. ............................. 435/6; 530/350; 536/22.1; 937/77; 937/78; 436/501; 514/2
[58] Field of Search ................................... 435/6; 935/77, 935/78; 530/350; 514/2; 536/22.1; 436/501

[56] References Cited

U.S. PATENT DOCUMENTS

| | | |
|---|---|---|
| 3,625,214 | 12/1971 | Higuchi . |
| 4,789,734 | 12/1988 | Pierschbacher . |
| 4,906,474 | 3/1990 | Langer et al. . |
| 4,925,673 | 5/1990 | Steiner et al. . |
| 5,525,495 | 6/1996 | Keene et al. . |

FOREIGN PATENT DOCUMENTS

WO 94/09792  5/1994  WIPO .

OTHER PUBLICATIONS

Ausubel et al., "Synthesizing Proteins In Vitro by Transcription and Translation of Cloned Genes," *Current Protocols in Molecular Biology*, pp. 10.17.1–10.17.5 (John Wiley & Sons, Inc., 1996).

Burd, et al., "Conserved Structures and Diversity of Functions of RNA–Binding Proteins," *Science* 265:615–621 (1994).

Current Protocol in Molecular Biology, Section VII, pp. 10.17.1–10.17.5 (John Wiley & Sons, Inc. 1989).

Gregoriadis, Chapter 14. "Liposomes", *Drug Carriers in Biology and Medicine* pp. 287–341 (Academic Press, 1979).

Johnstone, et al., "Production of Antibodies," *Immunochemistry in Practice*, pp. 30–34; pp. 234–240 (Blackwell Scientific Publications, 1987).

Malter, *Science* 240:668–670 (1989).

Rodriguez, et al., "Biotin–Labeled Riboprobes to Study RNA–Binding Proteins," *Biomethods* 7:215–225 (1996).

Rouault, et al., "The Iron–Responsive Element Binding Protein: A Method for the Affinity Purification of a Regulatory RNA–Binding Protein," *Proc. Natl. Acad. Sci. USA* 86:5768–5772 (1989).

Zaidi, et al., "*Nucleolin and heterogeneous nuclear*" *J. Bio. Chem.* 270(29):17292–17298 (1991).

Zaidi, et al., "Multiple Proteins Interact at a Unique cis–Element in the 3'–Untranslated Region of Amyloid Precursor Protein mRNA*" *J. Biol. Chem.* 269(39):24000–24006 (Sep. 1994).

*Primary Examiner*—Stephanie Zitomer
*Attorney, Agent, or Firm*—Clark & Elbing LLP; Kristina Bieker-Brady, Ph.D

[57] ABSTRACT

It has been discovered that a single set of conditions can be used to detect nearly every interaction of RNA binding proteins and RNA molecules. Prior to this discovery it was thought that each specific interaction required separate optimized conditions in order to be detected. Assays employing the disclosed universal conditions are useful for identifying RNA binding proteins that interact with specific RNA molecules of interest, detecting RNA molecules that interact with specific RNA binding proteins of interest, identifying RNA binding proteins active in certain cell types and under certain physiological conditions, identifying specific regions of an RNA molecule that interact with RNA binding proteins. Screening assays employing the disclosed universal conditions are useful for identifying compounds that modulate RNA/RBP interactions of interest.

22 Claims, 8 Drawing Sheets

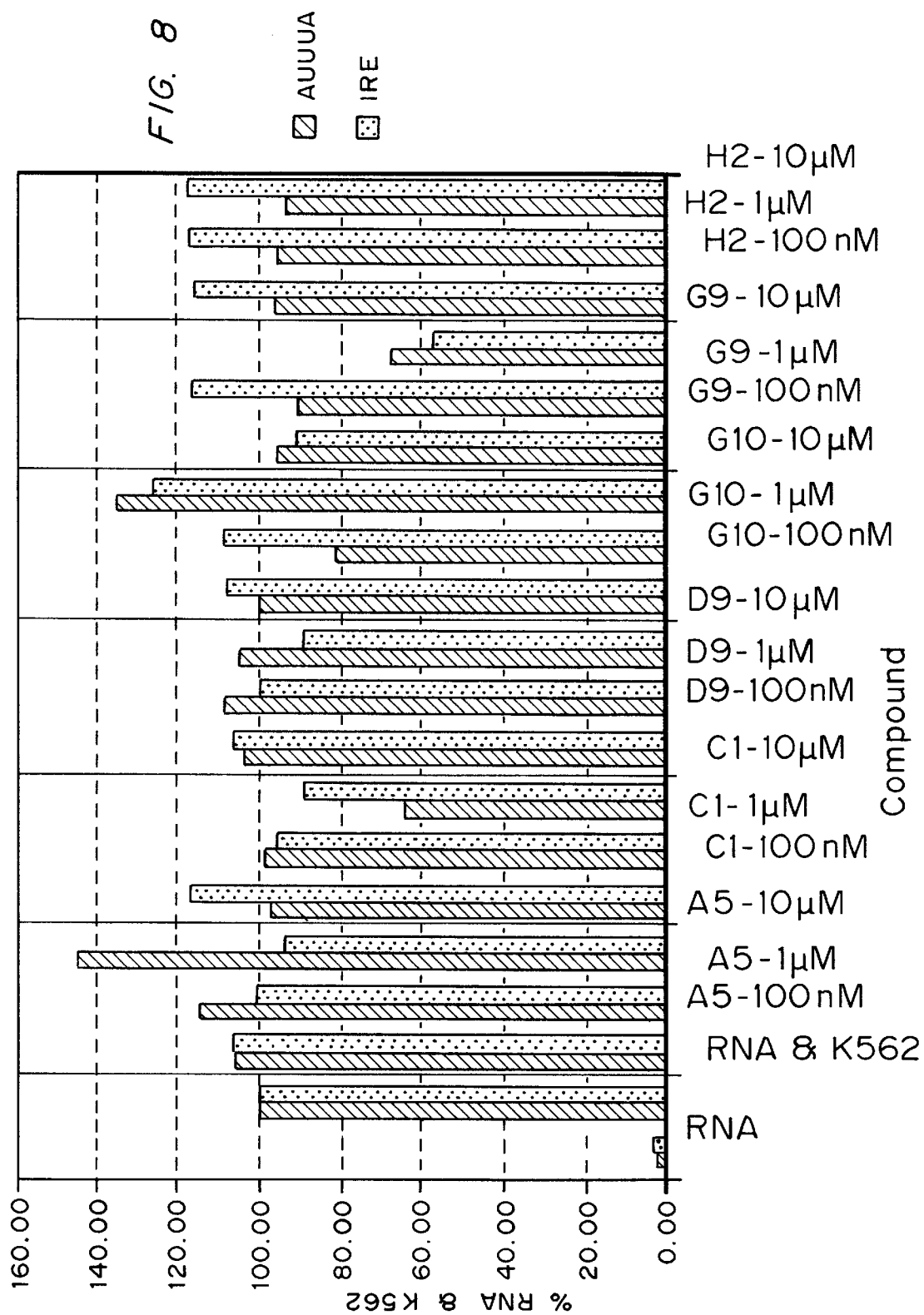

SYM 1301
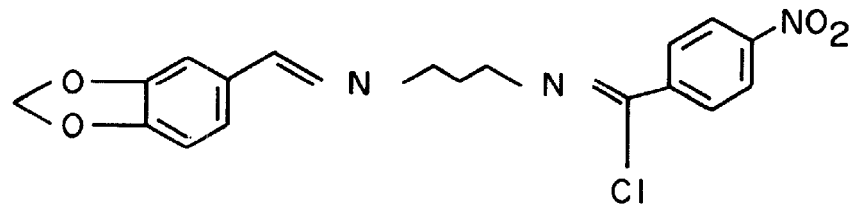
SYM 1405
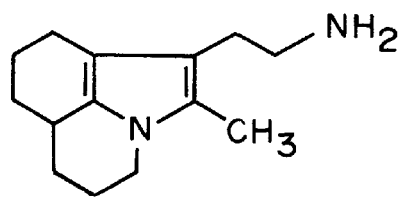
SYM 1710
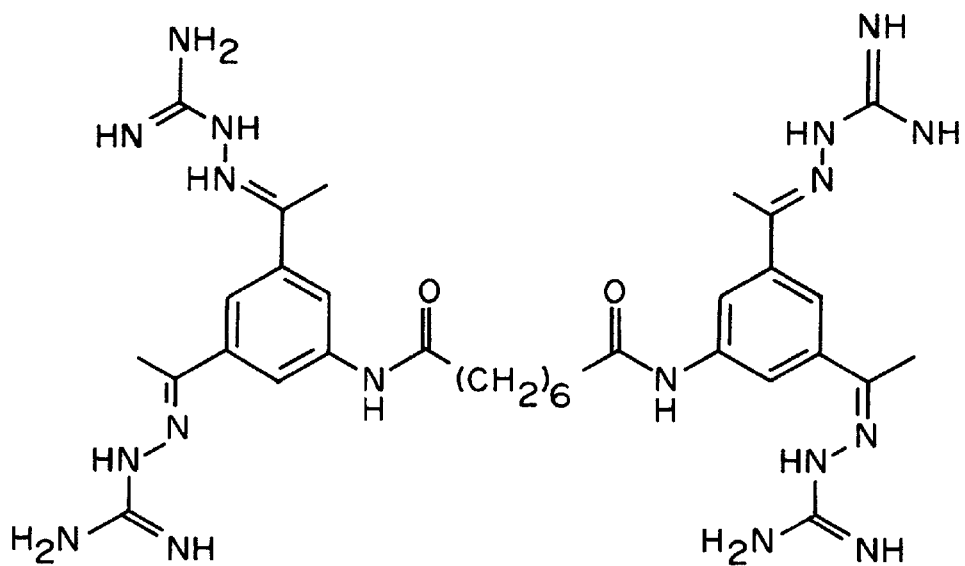
FIG. 10

6,004,749

METHOD FOR IDENTIFYING COMPOUNDS AFFECTING RNA/RNA BINDING PROTEIN INTERACTIONS

CROSS-REFERENCE TO RELATED APPLICATIONS

This application is a continuation-in-part of U.S. application Ser. No. 08/690,010, filed Jul. 31, 1996.

BACKGROUND OF THE INVENTION

The invention is in the area of screening assays for identifying compounds that affect interactions between RNA and RNA binding proteins.

The regulation of protein function can occur at a number of levels: transcriptional, post-transcriptional, or post-translational. The modulation of protein function is often critical for the treatment of disease. Recent work at modulating protein levels by altering transcriptional activity has resulted in preclinical research programs being established and licensing agreements being entered into. For example, Ligand Pharmaceuticals, Inc. (San Diego, Calif.) has entered into multiple drug discovery programs with large pharmaceutical companies based on their Signal Transducers and Activators of Transcription technology for use as anti-inflammatory, anti-cancer and hormone replacement therapies. In addition, Oncogene Science, Inc. (Uniondale, N.Y.) is using its proprietary gene transcriptional technologies to develop biopharmaceutical products for the treatment of cancer. Other companies, such as Signal Pharmaceuticals, Inc. (San Diego, Calif.) and Tularik, Inc. (San Francisco, Calif.) are developing small molecules that regulate transcription factors. While this approach holds promise, no compounds have yet to make it to clinical trials. The lack of specificity of transcription factors and requirement for nuclear localization are two concerns with this technology. In the first case, a drug affecting the binding of a transcription factor may affect transcription of many genes other than the target gene. In the second case, it is difficult to design a drug that both has the proper interaction with a targeted transcription factor and is transported into the nucleus where it exerts its effect. Inhibition of protein expression by targeting the RNA is an alternate approach involving anti-sense technology. The antisense technology has also generated much interest with several products in clinical trials (ISIS2105, ISIS2922 and ISIS2302). However, the major drawbacks with this approach are the cost of oligonucleotides, the ability to deliver the oligonucleotides into cells, and their inability to increase protein levels.

A major area of post-transcriptional regulation in eukaryotic cells involves the specific interaction of proteins with RNA. These RNA binding proteins (RBP) appear to mediate the processing of pre-mRNAs, the transport of mRNA from the nucleus to the cytoplasm, mRNA stabilization, the translational efficiency of mRNA, and the sequestration of some mRNAs. Recent studies have identified several RNA-binding motifs in a diversity of RBPs. The most common RNA binding protein motifs are the RNP motif, Arg-rich motif, RGG box, KH motif and double-stranded RNA-binding motif (for review see Burd and Dreyfuss, *Science* 265:615–621 (1994)). These motifs recognize both sequence and structure dependent RNA elements. In the case of the double-stranded RNA-binding motif, sequence recognition is unimportant. However, in addition to the double stranded structure, a positional effect for the double-stranded RNA may play a role in recognition (Bass, *Nucleic Acids Symposium* 33:13–15 (1995)) and some of these proteins may also require binding to Z-DNA prior to their activity on the double-stranded RNA (Herbert et al., *Proc. Natl. Acad. Sci. USA* 92:7550–7554 (1995)). In addition, other RNA binding proteins, such as AUBF (Malter, *Science* 246:664–666 (1989)) are likely to bind in a structure-independent manner.

Due to the clear importance of RNA/RBP interactions in the regulation of gene expression, these interactions would be an attractive target for drugs that affect them for modulation of protein levels in disease states. To fully exploit these interactions as therapeutic targets, however, requires a clear understanding of how these interactions affect expression, which RBPs are involved in the regulation of RNAs of interest, and the ability to study the modulating effects of potential drugs on the RNA/RBP interactions.

Many investigators have used mobility shift assays to detect RNA/protein interactions. However, the conditions established in one laboratory often fail to detect interactions of different molecules. In addition, the diversity of RNA structures and binding motifs in the protein have led numerous investigators to conclude that a single set of conditions would be impossible to define for detection of multiple different interactions. With more genes being identified as being post-transcriptionally regulated, a universal set of binding conditions would allow for the detection and characterization of the molecules involved in these interactions and ultimately would provide targets for which therapeutics could be developed. No such universal assay conditions have been previously described for the identification of RNA binding proteins, the RNA molecules and RNA-binding sites with which they interact, and the study of these interactions.

Due to the variety of RBPs and motifs it has generally been required that individual assay conditions be painstakingly worked out for each RNA/RBP combination, resulting in slow progress in studying known RBPs and their interactions and in slowed or prevented identification of additional RBPs and their RNA motifs. Clearly, some RNA/RBP interactions have gone undetected simply because the right assay conditions have never been tried. Thus, there is a need for more universal assay conditions which can be expected to detect the majority of specific RNA/RBP interactions.

Therefore, it is an object of the invention to provide an assay for detecting interactions between any RNA binding protein and its cognate RNA binding site.

It is a further object of the invention to provide a screening assay for identifying compounds that affect interactions between RNA molecules and RNA binding proteins.

SUMMARY OF THE INVENTION

It has been discovered that a single set of conditions can be used to detect nearly every interaction of RNA binding proteins and RNA molecules. Prior to this discovery it was thought that each specific interaction required separate optimized conditions in order to be detected. Assays employing the disclosed universal conditions are useful for identifying RNA binding proteins that interact with specific RNA molecules of interest, detecting RNA molecules that interact with specific RNA binding proteins of interest, identifying RNA binding proteins active in certain cell types and under certain physiological conditions, and identifying specific regions of an RNA molecule that interact with RNA binding proteins. Screening assays employing the disclosed universal conditions are useful for identifying compounds that modulate RNA/RBP interactions of interest.

BRIEF DESCRIPTION OF THE DRAWINGS

FIG. 8 is a graph of the amount of radioactively labeled RNA retained on a filter (expressed in percent of the amount of RNA retained on a filter in a reference binding solution) following loading of various binding solutions. Alternate columns correspond to binding solutions containing radioactively labeled AUUUA RNA or IRE RNA, either alone or including various other components. The first two column represents binding solutions without RNA binding protein. The remaining columns represent binding solution containing RNA binding protein (K562 extract). Columns 5 through 40 correspond to binding solutions including the indicated amount of the indicated test compound.

FIG. 10 is a diagram of the structures of compounds SYM 1301, SYM 1405, and SYM 1710.

DETAILED DESCRIPTION OF THE INVENTION

Figure 1:
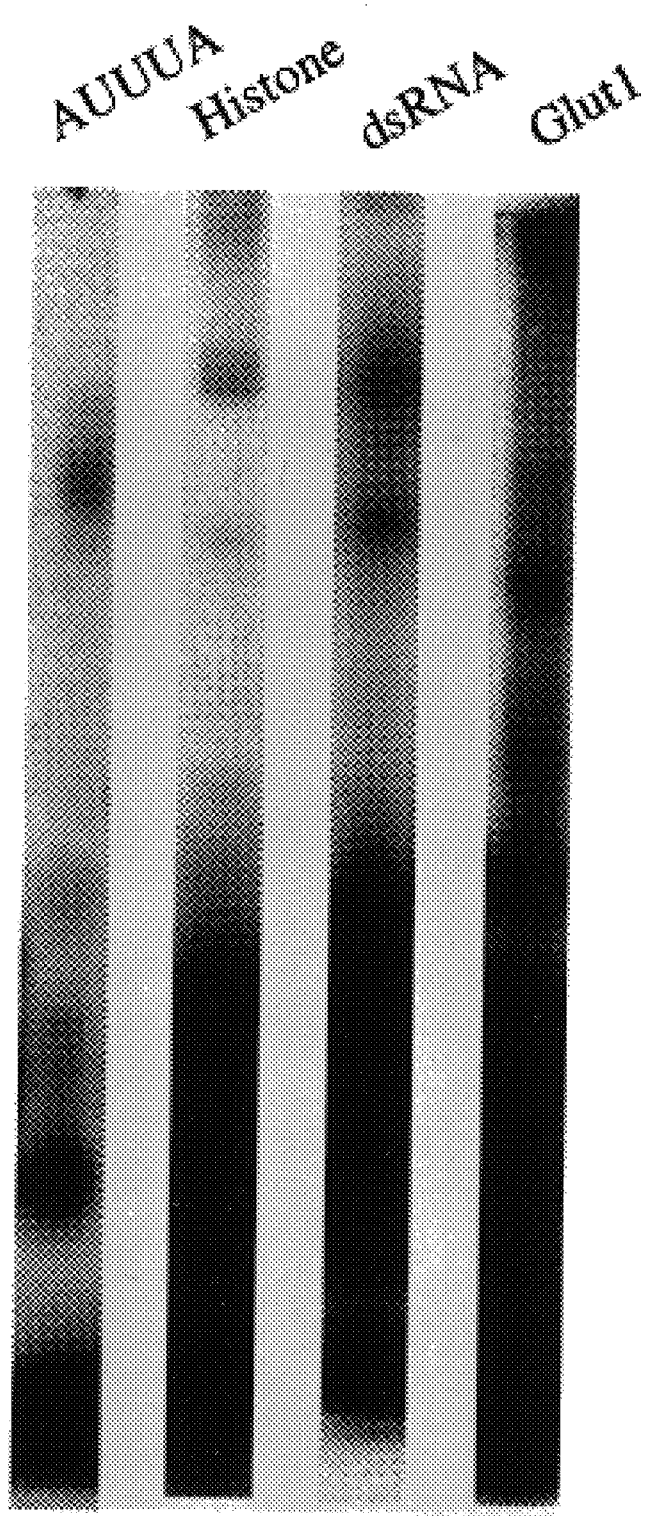
FIG. 1 is a digitized image of a gel mobility shift assay gel showing the relative migration of radioactive RNA molecules. Four different radioactive RNA molecules, AUUUA, histone, double-stranded RNA (dsRNA), and the glucose transporter type 1 (Glut1) 5' untranslated region, were incubated with either SH-SY5Y or CHL/260 protein extract and altered mobility of the RNA molecules in a gel is indicated by slow migrating radioactive bands or smears.

Disclosed are universal conditions and procedures that can be applied to any RNA molecule and any RNA binding protein to detect interactions between them. The basic detection procedure can be adapted to detect interactions between RNA binding proteins and RNA molecules in bulk, interactions between RNA binding proteins and a specific RNA molecule, and interactions between RNA molecules and a specific RNA binding protein. The detection procedure can thus be used to, for example, detect all of the RNA binding proteins present in a sample, such as a cell or tissue extract, with a specific RNA molecule, such as the transcript from a gene of interest. Similarly, the detection procedure can be used to detect all of the RNA molecules present in a sample, such as a cell or tissue extract, with a specific RNA binding protein.

The detection procedure, and a kit therefor, is useful as a research tool, both for identifying interactions between RNA molecules and RNA binding proteins, and for identifying compounds that modulate such interactions. Compounds identified in such a screening assay could be useful for regulating the expression of RNA molecules of interest. The importance of interactions between RNA molecules and RNA binding proteins was described above. All of the uses can be accomplished by applying the basic detection procedure and specific adaptions of the basic detection procedure as described herein.

It has been discovered that a single set of conditions can be used to detect nearly every interaction of RNA binding proteins and RNA molecules. These conditions allow detectable complexes between RNA binding proteins and RNA molecules and are thought to mimic physiological conditions in cells where such interactions normally occur. Prior to this discovery it was thought that each specific interaction required separate optimized conditions in order to be detected.

As used herein, interactions between RNA binding proteins and RNA molecules which are referred to as "possible" are intended to mean those interactions which are specific and which occur under at least one set of conditions (e.g. in vivo or optimized binding assay conditions). In the context of the disclosed universal method of detecting interactions between RNA binding proteins and RNA molecules, the method will detect a majority of the interactions between RNA binding proteins and RNA molecules which are possible. The meaning of the term "specific interaction" is generally understood to mean interactions that are based on specific characteristics of the interacting molecules and not on general characteristics. For example, certain RNA binding proteins recognize and bind specifically to sites in RNA molecules having the nucleotide sequence AUUUA. This is a specific interaction. Conversely, some proteins bind RNA molecules in general (i.e. non-specifically) based on the general chemical characteristics of all RNA molecules. In general, an interaction can be identified as a non-specific interaction by determining that the interaction can be prevented in the presence of a non-specific competitor. Preferred assay conditions for the disclosed universal assay are those that allow detection of interactions between proteins in an SH-SY5Y protein extract and amyloid precursor protein 3' untranslated region, four repeats of the AUUUA sequence from unstable RNAs (Malter, Science 240:668–670 (1989), and poly(A), since detection of such diverse RNA/RBP interactions is considered indicative of deductibility of many RNA/RBP interactions.

I. Components

A. Binding Solution

Interactions between RNA binding proteins and RNA molecules are facilitated in a binding solution. The binding solution contains one or more RNA molecules and buffer components. The buffer components include a buffer, a monovalent cation, a divalent cation, a reducing agent, and a density agent. It is preferred that the buffer is Bis-Tris Propane at a pH of about 8.5 and at a concentration of about 7.5 mM, the monovalent cation is $K^+$ at a concentration of about 50 mM, the divalent cation is $Mg^{++}$ at a concentration of about 1 mM, the reducing agent is dithiothreitol at a concentration of about 0.2 mM, and the density agent is glycerol at a concentration of about 10 percent (v/v).

These conditions have been optimized to be universally applicable. It is most preferred that the optimum conditions be used. However, one, or less preferably two, of the buffer components can be varied in the manner disclosed below. For varying certain buffer components, it is preferred that (1) the buffer is HEPES, Tris, or Bis-Tris Propane, each at a pH between about 8 and 10 and at a concentration of between about 5 and about 100 mM, (2) the monovalent cation is $K^+$, $Na^+$, or $NH_4^+$, each at a concentration of between 0 and about 100 mM, (3) the divalent cation is $Mg^{++}$, $Ca^{++}$, or $Fe^{++}$, each at a concentration of between 0 and about 5 mM, (4) the reducing agent is dithiothreitol or β-mercaptoethanol, at a concentration of between 0 and about 1 mM, and the density agent is glycerol or polyethylene glycol at a concentration of between 0 and about 20 percent (v/v).

For most RNA molecules, the reducing agent does not appear to be critical, although there is a trend to slightly better binding in the presence of a reducing agent, preferably DTT. However, in some cases the reducing agent makes a significant difference in the detection of interactions. Accordingly, the use of a reducing agent is preferred. A density agent does not appear to be required for detecting the interaction between RNA molecules and RNA binding proteins. However, when interactions are analyzed by gel mobility shift, the presence of a density agent does enhance the quality of the bands. Accordingly, the use of a density agent is preferred.

The binding solution can include other components that aid in the formation of specific interactions. For example, a competitor of non-specific RNA/protein interactions can be added to reduce the background of non-specific interactions. Poly r(G), tRNA, and heparin, are preferred competitors of non-specific RNA/protein interactions.

It is intended that a concentration range stated as between 0 and about a specific concentration does not encompass a concentration of zero but does encompass the specific concentration and concentrations up to about 10% greater than the specific concentration. It is also intended that a concentration range stated as between about a first specific concentration and about a second specific concentration encompasses the first specific concentration, concentrations up to about 10% lower than the first specific concentration, concentrations between the first and second specific concentrations, the second specific concentration, and concentrations up to about 10% greater than the second specific concentration. It is intended that a concentration range stated as from a first specific concentration to a second specific concentration encompasses the first specific concentration, concentrations between the first and second specific concentrations, and the second specific concentration. It is also intended that a concentration range stated as from 0 to a specific concentration encompasses a concentration of zero, concentrations between zero and the specific concentration, and the specific concentration.

Unless otherwise noted, all concentrations of buffer components are intended to be the final concentration of these components in a completely formed binding solution. The binding buffer can be formed by any combination of components that results in the intended final concentration. For example, a binding solution can be formed by mixing together, with other components of the binding solution, a single stock solution of buffer components, separate stock solutions of buffer components, or separate stock solutions of combinations of some of the buffer components. It is also intended that the final concentration of buffer components can be achieved by mixing different solutions each containing a part of the total amount of a given component. For example, part of the divalent cation can be added as part of a stock solution and part can be added with the RNA.

It is preferred that the concentration of extraneous compounds be kept to a minimum in binding solutions. It is understood, however, that samples of RNA binding proteins and RNA molecules may contain additional compounds. The concentration in the binding solution of such compounds can be reduced by, for example, diluting the sample to the greatest extent possible when forming the binding solution.

B. RNA Binding Proteins

RNA binding proteins for use in the disclosed method can be part of a crude cellular or nuclear extract, partially purified, or extensively purified. RNA binding proteins can be used either in isolation or in combination with one or more other RNA binding proteins. Preferably, three or more, four or more, or five or more RNA binding proteins are used. When the goal is to identify RNA binding proteins in a sample, it is preferred that the sample be an unpurified or partially purified extract so that the largest variety of RNA binding proteins will be present. When the goal is to identify RNA molecules, or portions of an RNA molecule, that interact with a specific RNA binding protein, it is preferred that the RNA binding protein be substantially purified.

RNA binding proteins can be prepared using known methods for preparing cellular extracts and for purifying proteins. Methods for preparing extracts containing RNA binding proteins and for purifying known RNA binding proteins are described in, for example, Ashley et al., *Science* 262:563–566 (1993), Rouault et al., *Proc. Natl. Acad. Sci. USA* 86:5768–5772 (1989), Neupert et al., *Nucleic Acids Research* 18:51–55 (1990), Zhang et al., *Molecular and Cellular Biology* 13:7652–7665 (1993), and references cited in Burd and Dreyfuss, *Science* 265:615–621 (1994). Individual RNA binding proteins can also be produced recombinantly using known techniques. DNA encoding RNA binding proteins can be obtained from known clones, by synthesizing a DNA molecule encoding an RNA binding protein with a known amino acid sequence, or by cloning the gene encoding the RNA binding protein. Techniques for recombinant expression of proteins and methods for cloning genes encoding known proteins are described by, for example, Sambrook et al., *Molecular Cloning* (Cold Spring Harbor Laboratory, 1989).

Detection of interactions between RNA binding proteins and RNA molecules can be facilitated by attaching a detectable label to the RNA binding protein. Generally, labels known to be useful for proteins can be used to label RNA binding proteins. Preferred labels for RNA binding proteins are $^{125}I$, $^3H$, and $^{35}S$. When the RNA binding protein is made recombinantly, it can be labeled by incorporation of labeled amino acids. Techniques for labeling and detecting labeled proteins are well known and are described in, for example, Sambrook et al., and Ausubel et al., *Current Protocols in Molecular Biology* (John Wiley & Sons, Inc., 1996). Detection of RNA binding proteins can also be accomplished with antibodies specific for the RNA binding protein. The production and use of antibodies for this purpose is well known and is described in, for example, Johnstone and Thorpe, *Immunochemistry in Practice* (Blackwell Scientific Publications, 1987).

C. RNA Molecules

RNA molecules for use in the disclosed method can be part of a crude cellular or nuclear extract, partially purified, or extensively purified. RNA molecules can also be made by in vitro transcription or by direct synthesis. RNA molecules can be used either in isolation or in combination with one or more other RNA molecules. Preferably, three or more, four or more, or five or more RNA molecules are used. When the goal is to identify RNA molecules in a sample, it is preferred that the sample be an unpurified or partially purified extract so that the largest variety of RNA molecules will be present. When the goal is to identify RNA binding proteins that interact with a specific RNA molecules, it is preferred that the RNA molecules be substantially purified. For this purpose, it is most preferred that the RNA molecule be produced in vitro.

RNA molecules can be prepared using known methods for preparing cellular extracts and for purifying RNA. Methods for preparing extracts containing RNA molecules are described in, for example, Sambrook et al., and Ausubel et al. Individual RNA molecules can also be produced recombinantly using known techniques, by in vitro transcription, and by direct synthesis. For recombinant and in vitro transcription, DNA encoding RNA molecules can be obtained from known clones, by synthesizing a DNA molecule encoding an RNA molecule, or by cloning the gene encoding the RNA molecules. Techniques for in vitro transcription of RNA molecules and methods for cloning genes encoding known RNA molecules are described by, for example, Sambrook et al.

Detection of interactions between RNA binding proteins and RNA molecules can be facilitated by attaching a detectable label to the RNA molecule. Generally, labels known to be useful for nucleic acids can be used to label RNA molecules. Examples of suitable labels include radioactive isotopes such as $^{33}P$, $^{32}P$, and $^{35}S$, fluorescent labels such as fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7, and biotin.

Labeled nucleotides are the preferred form of label since they can be directly incorporated into the RNA molecules during synthesis. Examples of detection labels that can be incorporated into amplified RNA include nucleotide analogs such as BrdUrd (Hoy and Schimke, *Mutation Research* 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.* 22:3226–3232 (1994)). A preferred nucleotide analog label for RNA molecules is Biotin-14-cytidine-5'-triphosphate. Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into RNA molecules, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [$3.3.1.1^{3,7}$]decane]-4-yl) phenyl phosphate; Tropix, Inc.).

II. Method

The basic method for detecting interactions between RNA molecules and RNA binding proteins involves forming a binding solution containing the RNA molecules and 1× binding buffer, heating the binding solution to denature the RNA molecules, cooling the binding solution to the reaction temperature, adding the RNA binding proteins to the binding solution, and detecting the interactions between the RNA molecules and the RNA binding proteins.

A. Forming the Binding Solution

The binding solution contains one or more RNA molecules, buffer components, and non-specific competitors. The buffer components include a buffer, a monovalent cation, a divalent cation, a reducing agent, and a density agent. The binding solution is formed by combining and/or mixing together the constituents of the binding solution in any manner that results in a binding solution having the required composition. The binding buffer can be formed by any combination of components that results in the intended final concentration. For example, a binding solution can be formed by mixing together, with other components of the binding solution, a single stock solution of buffer components, separate stock solutions of buffer components, or separate stock solutions of combinations of some of the buffer components. It is also intended that the final concentration of buffer components can be achieved by mixing different solutions each containing a part of the total amount of a given component. For example, part of the divalent cation can be added as part of a stock solution and part can be added with the RNA. Thus, the manner in which the final composition of the binding solution is arrived at is not critical. It is intended that any combination of solutions and components that achieves this result is encompassed by this step.

B. Heating and Cooling the Binding Solution

The formed binding solution is heated and cooled in order to denature any higher order structure in the RNA molecules. Such structures can make the RNA molecules less accessible to the RNA binding proteins. When using RNA molecules purified from natural sources, it is also possible that other molecules can remain bound to the RNA. The heating step can serve to release such molecules. The heating and cooling step involves subjecting the binding solution to a heat source until it reaches a sufficient temperature, and then allowing the solution to cool to the reaction temperature. The temperature to which the binding solution is heated can be any temperature that will substantially denature the RNA molecules present in the binding solution. It is understood that different temperatures will be sufficient for different RNA molecules. For example, shorter RNA molecules and RNA molecules with a low GC content will, in general, be substantially denatured at lower temperatures. However, it is preferred that a single temperature be used for the heating step. In this case, it is preferred that a temperature sufficient to substantially denature RNA molecules in general be used. A preferred temperature is 80–85° C. After allowing the solution to cool to the reaction temperature, the RNA binding protein is added to the binding solution prior to incubation at the appropriate temperature for RNA-protein binding, preferably 37° C.

C. Detecting Interactions

Interactions between RNA binding proteins and RNA molecules can be detected using any suitable procedure. It is preferred that detection involve separation of interacting RNA molecules and RNA binding proteins from non-interacting RNA molecules. This can be accomplished, for example, by separating components in the binding solution on the basis of size or physical properties. Two preferred methods of separation and detection of interacting RNA molecules and RNA binding proteins are filter binding and gel mobility shift.

1. Filter binding. Filter binding involves trapping interacting molecules on a filter while non interacting molecules pass through the filter. This procedure is known to those of skill in the art. For example, prewet nitrocellulose filters are equilibrated in 1× binding buffer. The binding reaction is then applied to the filter by vacuum filtration to remove unbound RNA. The filter is washed in 1× binding buffer, scintillation cocktail is added and the amount of protein-bound RNA is determined by scintillation counting.

For assays involving filter binding, it is also preferred that a non-interacting control assay be performed. Such a control is used to determine the detectable signal retained in the absence of specific RNA/RNA binding protein interaction. Preferably, such a non-interacting control assay is performed by substituting a mutant RNA molecule—one that does not interact specifically with the RNA binding protein—for the RNA molecule used in corresponding binding assays. The level of detectable signal bound to the filter in the non-interacting control indicates the contribution of background, or non-specific, signal present in the level of detectable signal measured for the binding assays. In the high throughput screening assay, the non-interacting control is also a control for the control assays (that is, assays not containing a test compound). It is expected that the level of background signal can be reduced by including a low concentration of detergent in the wash buffer. Preferred detergents for this purpose are Tween 20 and Triton N-101. For a given set of test reactions, a non-interacting control assay can be used to determine the effectiveness of the washes.

It is preferred that the concentration of RNA binding protein in the disclosed assays be at least 0.1 $\mu g/\mu l$ or between 0.1 $\mu g/\mu l$ and 1.0 $\mu g/\mu l$. For assays using filter binding, the filter is preferably either pure nitrocellulose or a mixed cellulose ester (mixed cellulose acetate). For the disclosed assay, the mixed cellulose ester filters bound more counts than pure nitrocellulose. For the filters, a 0.2 $\mu m$ pore size (8000 dalton MW cutoff) is most preferred, although MCA filter plates with a 0.45 $\mu m$ pore size (20,000 dalton MW cutoff) are also preferred. The lower molecular weight cutoff allows detection of binding interactions between RNA and small molecular weight molecules. For the high throughput screening assay, it is preferred that the binding reactions are carried out in 96 well polystyrene plates in a final volume of 10 or 100 $\mu l$. After binding, the samples are loaded onto a 96 well Millipore filter plate.

For assays using filter binding, it is preferred that, following incubation and prior to loading unto the filter, the reactions in a final volume of 10 $\mu l$ be brought to a larger final volume, most preferably a final volume of 110 $\mu l$, by the addition of a solution, referred to as the dilution solution. Preferred dilution solutions include 1× BTP binding buffer with glycerol, 1× BTP without glycerol, TE, PBS, and TCA, with 1× BTP without glycerol being most preferred. It is most preferred that the dilution solution have the same buffer components (preferably at the same final concentration) as used in the binding solution except lacking the density agent. This dilution allows more even loading of the sample on the filter plate. It is contemplated that the preferred final volume used should differ depending on the area of filter to which the assay solution will be applied. Thus, assays in which larger filter areas are used are preferably brought to a final volume greater than 110 $\mu l$ and assays in which smaller filter areas are used are preferably brought to a final volume less than 110 $\mu l$.

It is preferred that the assay solution be loaded onto the filter under vacuum. After loading, it is preferred that the filters be washed, preferably two times. Preferred wash buffers (also referred to as the wash solution) include 1× BTP binding buffer with glycerol, 1× BTP without glycerol, TE, PBS, and TCA, with 1× BTP without glycerol being most preferred. It is most preferred that the wash buffer have the same buffer components (preferably at the same final concentration) as used in the binding solution except lacking the density agent. It is also preferred that the wash buffer be cold (that is, below room temperature).

2. Gel mobility shift. Gel mobility shift involves resolving interacting and non-interacting RNA molecules and RNA binding proteins on a gel by electrophoresis and visualizing the location and amount of components that migrate to different extents. Interacting RNA molecules and RNA binding proteins tend to migrate less in the gel than non-interacting molecules by virtue of their greater mass. Gel mobility shift assays can be performed as follows. After incubation of the binding reaction, 6× loading buffer (30% glycerol, 0.25% xylene cyanol, 0.25% bromophenol blue) is added to a final concentration of 1×. The reaction is then loaded into the wells of a polyacrylamide gel (generally 4 to 8%) prepared in TBE buffer (90 mM Tris-borate, 2 mM EDTA, pH 8). The protein-bound RNA is separated from the unbound RNA by applying a constant voltage (150 to 175 V) to the gel and allowing the gel to run until the bromophenol blue has reached the bottom of the gel. The gel is the dried in vacuo at 80° C. The unbound RNA and the protein-bound RNA is then visualized autoradiographically. In cases where it is desirable to know the molecular weight of the RNA-protein complex, the binding reaction is subjected to ultraviolet light to covalently crosslink the complex. 6× loading buffer (3.75 M Tris, 30% βME, 13.8% SDS, 30% glycerol, pH 6.8) is added to the crosslinked reaction at a final concentration of 1× and the mixture is loaded onto an SDS-polyacrylamide gel (generally 8 to 12%). The gel is run in a Tris-glycine buffer (25 mM Tris, 192 mM glycine, 0.1% SDS) at 30 mA until the molecular weight markers are adequately separated. The gel is dried and the RNA-protein complex visualized autoradiographically.

3. Ribonuclease digestion. For some assays it may be desirable to eliminate those RNA molecules, or those regions of an RNA molecule, that are not involved in an interaction with RNA binding proteins. For example, when a large RNA molecule is used in the assay, binding of an RNA binding protein might result in an RNA/protein complex only slightly larger than the RNA molecule alone. When detecting such a complex by gel mobility shift, the resulting shift may not be easily detectable. When detecting such a complex by filter binding, the RNA molecule alone may be sufficiently large to be retained by the filter. Such potential problems can be mitigated by digesting RNA not involved in interactions. This is easily accomplished by subjecting the binding solution to ribonuclease digestion. Only the unbound or non-interacting RNA will be digested. The regions of RNA bound by RNA binding proteins will be protected from digestion by the protein.

D. Identifying RNA Molecules and RNA Binding Molecules That Interact With Specific RNA Binding Proteins and RNA Molecules Identification of RNA molecules that interact with a specific RNA binding protein can be accomplished by forming a binding solution comprising one or more RNA molecules, and buffer components comprising a buffer, a monovalent cation, a divalent cation, a reducing agent, and a density agent, adding the specific RNA binding protein, and detecting interactions between the one or more RNA molecules and the RNA binding protein. Those RNA molecules that interact can be identified by specific sequence analysis. An assay of this type can be used to identify all those RNA molecules in a given sample which are specific for an RNA binding protein of interest. The identification of such RNA molecules can lead to the identification of genes encoding RNA molecules regulated by the RNA binding molecules of interest.

In a similar way, RNA binding proteins that interact with a specific RNA molecule can be identified by forming a binding solution comprising the RNA molecule of interest, and the buffer components, adding one or more RNA binding proteins, and detecting interactions between the one or more RNA binding proteins and the RNA molecule.

E. Identifying Genes Encoding RNA Molecules That Interact With RNA Binding Proteins The genes encoding RNA molecules that interact with RNA binding proteins can be identified by synthesizing a labeled cDNA from the RNA molecule and using the cDNA to screen a library of genes thought to contain the gene encoding the RNA molecule. The gene encoding the RNA molecule can then be identified by sequence analysis. The identity of the gene can be confirmed by determining the intron-exon structure of the gene, cloning the exons into a vector and transcribing the RNA in vitro. The in vitro transcribed RNA can then be used to form a binding solution, and the interactions with the RNA binding proteins can be detected and compared with the interactions of the original RNA and RNA binding protein. The gene is confirmed as encoding the RNA molecule if the interactions between the test RNA and the RNA binding proteins are substantially the same as those of the original RNA and the RNA binding proteins. Procedures for all of these manipulations are well established and known to those of skill in the art and/or are described herein.

F. Identifying Genes Encoding RNA Binding Proteins

The genes encoding RNA binding proteins that interact with RNA molecules can be identified by isolating the binding protein and determining a portion of the amino acid sequence. This sequence can then be used to generate peptides which in turn can be used to produce antibodies to the RNA binding protein. Additionally, or alternatively, the peptide sequence can be reverse translated to generate a cDNA probe. The probes or antibodies can then be used to screen a cDNA library (expression library when antibodies are used) and resulting cDNA clones used to screen a genomic library. The gene encoding the RNA binding protein can then be identified by sequence analysis. The identity of the gene can be confirmed by determining the intron-exon structure of the gene, cloning the exons into a vector and performing in vitro transcription/translation to express the protein or by expressing the protein in vivo. The expressed protein can then be added to the binding solution, the interactions with the RNA molecules detected and compared with the interactions of the original RNA binding protein and RNA molecules. The gene is confirmed as encoding the RNA binding protein if the interactions between the test protein and the RNA molecules and the original protein and RNA molecules are substantially the same. Procedures for all of these manipulations are well established and known to those of skill in the art and/or are described herein.

G. Identifying Regions In RNA Molecules That Interact With RNA Binding Proteins

Regions in RNA molecules that interact with RNA binding proteins can be identified by forming a binding solution comprising (1) an RNA molecule from a subset of RNA molecules consisting of successively smaller fragments of a larger RNA molecule previously identified to be involved in an RNA-protein interaction, or (2) an RNA molecule containing one or more mutations or deletions in a previously identified RNA molecule involved in an RNA-protein interaction, buffer components comprising a buffer, a monovalent cation, a divalent cation, a reducing agent, and a density agent, and non-specific competitors, adding one or more RNA binding proteins, and detecting the interaction between the RNA molecule and the RNA binding proteins. By comparing which RNA molecules interact with the binding proteins to those which do not interact, the region of the RNA molecule involved in the interaction can be identified. An assay of this type can identify all the regions in an RNA molecule involved in an interaction with an RNA binding protein as well as identifying the specific nucleotides that interact with the RNA binding protein.

H. Identifying Regions in RNA Binding Proteins That Interact With RNA Molecules

Regions in RNA binding proteins that interact with RNA molecules can be identified by forming a binding solution comprising one or more RNA molecules, buffer components comprising a buffer, a monovalent cation, a divalent cation, a reducing agent, and a density agent, and non-specific competitors, and adding one or more fragments of an RNA binding protein that were obtained by peptidase digestion of an RNA binding protein or by peptide synthesis, and detecting the interactions of the RNA binding protein peptides with the RNA molecules. This is feasible since the portion of an RNA binding protein that interacts with an RNA molecule is generally a self-contained domain. By comparing which peptides are involved in an interaction with an RNA molecule and which are not, the region of the RNA binding protein involved in the interaction can be identified. Identification of the specific amino acids involved in the interaction of the RNA binding protein with the RNA molecules can be accomplished by making mutations in the peptide fragments that interact with the RNA molecules and testing the mutated peptides for interactions with RNA molecules. The amino acids that are involved in the interaction of the RNA binding protein with the RNA molecule will be identified by the mutated peptides that do no interact with the RNA molecule.

I. Screening For Compounds That Modulate Interaction Of RNA Molecules And RNA Binding Proteins Identification of compounds that modulate the interaction of RNA molecules and RNA binding proteins can be accomplished by including one or more test compounds in the binding solution comprising the RNA molecules of interest, the RNA binding proteins of interest, and buffer components, and detecting the interaction between the RNA molecules and the RNA binding proteins. Test compounds that modulate or affect the interaction between the RNA molecules and RNA binding proteins can be identified by comparing the interactions in the binding solution that does not contain the test compound with the interactions in the binding solution containing the test compounds. Binding solutions that include one or more test compounds are referred to herein as test solutions. Binding solutions that do not include a test compound are referred to herein as control solutions. Compounds that modulate the interaction will be identified if the interactions in the two solutions differ. An assay of this type can be used to identify compounds that modulate or affect the interaction by binding to the RNA molecules or by binding to the RNA binding proteins in a given sample. By delivering an identified compound to a cell in which an RNA molecule of interest, or a related RNA molecule, is expressed, the function or action of the RNA molecule in the cell can be affected due to the modulation or effect the compound has on the interaction of an mRNA molecule and RNA binding proteins. For example, where an interaction between an mRNA molecule and an RNA binding protein controls the translation of the mRNA, a compound identified as affecting that interaction in the disclosed assay can be used to affect the translation of the mRNA via its effect on the interaction. Identified compounds can be used to affect the function or expression of an RNA molecule in a cell in vivo, ex vivo, or in vitro. The identification of such compounds can also lead to the development of therapies to treat a variety of diseases. Such compounds can also be used as research tools to study the significance, nature, or mechanism of RNA function or expression in a cell.

1. High throughput screening assay. The disclosed universal assay conditions can be used in a screening assay to identify compounds which affect a RNA/RNA binding protein interaction of interest. Such screening assays can be designed to allow simultaneous assessment of the effect of numerous test compounds on the interaction of interest. For this purpose, it is preferred that the interactions be detected by filter binding. Simultaneous filter binding assays are preferably performed by simultaneous filtering of binding solutions in an apparatus having separate wells, holes, slots, or other compartments which can hold separate binding solutions. A preferred apparatus is a multi-well filter binding apparatus such as the MultiScreen filter plate of Millipore. It is also contemplated that multiple multi-well or multi-sample assays can be performed simultaneously.

In general, high throughput screening can be performed as follows. First, a set of one or more test solutions is formed, where each test solution includes one or more RNA molecules and buffer components. Prior to addition of the test compound, the RNA is heated for a time and to a temperature sufficient to denature the RNA molecule(s), and slowly cooled. After addition of the test compound, one or more RNA binding proteins are added to the test solutions, and interactions between the RNA molecule(s) and the RNA binding protein(s) in the test solutions are detected. One of the test compounds is included in the test solution. To determine whether the test compounds have an effect on the interactions between the RNA molecule(s) and the RNA binding protein(s) a control solution is formed, heated, and cooled as with the test solutions, except that no test compound is present in the control solution. The RNA binding protein(s) are added to the control solution, and interactions between the RNA molecule(s) and the RNA binding protein (s) in the control solution are detected. By comparing the interactions detected in the test solutions with those detected in the control solution, it can be determined if a given test compound has an effect on the interactions. A test compound is identified as a compound having an effect on interactions between the RNA molecule(s) and the RNA binding protein (s) if the interactions detected in the control solution and the interactions detected in the test solution containing the test compound differ.

The test compound can be added to the test solution at almost any time, for example, during formation of the test solution, prior to adding the RNA binding protein, or with the RNA binding protein. It is preferred that the test compound is mixed with either the RNA molecule or the RNA binding protein prior to their addition to the test solution.

The assay using the control solution can be performed separately from, or together with, the assays of the test solutions. When performed separately, the control solution assay can be performed either before, after, or simultaneous with the test solution assays. It is preferred that the control solution assay be performed together and simultaneous with the test solution assays.

As used herein a set of test solutions refers to one or more test solutions which are related to each other by having the same RNA binding protein(s), RNA molecule(s), and buffer components. The test solutions within a set of test solutions preferably differ from each other in the test compound present in the test solution. It is contemplated and preferred that a single control solution, or a single form of control solution, be used for comparison of interactions detected in an entire set of test solutions. For this purpose it is preferred that the control solution have the same RNA binding protein (s), RNA molecule(s), and buffer components as the test solutions in the set. Multiple sets of test solutions, and a control solution for each set, can also be assayed together in a high throughput assay. For this purpose it is preferred that either or both of the RNA binding protein(s) or the RNA molecule(s) differ between each set of test solutions. For assays involving such multiple sets of test solutions, it is preferred that each set of test solutions use the same set of test compounds.

Preferred relationships between test solutions, sets of test solutions, and control solutions, as described above, can be illustrated with the following schematic examples. In the following examples, different RNA molecules or sets of RNA molecules (a given solution can contain a single RNA molecule or multiple RNA molecules) are referred to R1, R2, R3, etc. Different RNA binding proteins are referred to as P1, P2, P3, etc. Test compounds are referred to as C1, C2, C3, etc. Buffer components, as a group of components in a given solution, are referred to as B1, B2, B3, etc.

Three sets of test solutions, referred to as set 1, set 2, and set 3, are set up using the following components:

|  | Set 1 | Set 2 | Set 3 |
| --- | --- | --- | --- |
| RNA | R1 | R2 | R3 |
| Protein | P1 | P2 | P3 |
| Buffer | B1 | B1 | B1 |

For each set, a different control solution is set up using these same components. Thus, each set is designed to assess the effect of test compounds on a different RNA/RNA binding protein interaction (or group of interactions). A different test compound can be included in each test solution in each set as follows:

| Test solution | Set 1 | Set 2 | Set 3 |
| --- | --- | --- | --- |
| 1 | C1 | C1 | C1 |
| 2 | C2 | C2 | C2 |
| 3 | C3 | C3 | C3 |
| 4 | C4 | C4 | C4 |
| ... | ... | ... | ... |
| 92 | C92 | C92 | C92 |
| 93 | C93 | C93 | C93 |
| 94 | C94 | C94 | C94 |
| 95 | C95 | C95 | C95 |

No test compound is added to the control solutions. As can be seen, in this example, the same bank of 95 test compounds are tested for an effect on each of the three RNA/RNA binding protein interactions. Similar groups of assays could be performed using a different set of test compounds, or a partially overlapping set of compounds. The entire group of assays described above can be performed simultaneously and, preferably, is automated. The number of assays in any set of test assays can be increased to accommodate as many test compounds as desired. In such cases, of course, it is preferred that the set of test assays be divided into manageable groups, based on, for example, the number of wells in a multi-well filter apparatus. It is contemplated that the disclosed method can be performed using devices and apparatus designed to accommodate a large number of test assays.

2. Preferred modes of identifying compounds. It is preferred that interactions be detected in an automated manner using, for example, automated detection and comparison of interaction signals. Where the RNA molecule(s) or the RNA binding protein(s) are labeled with a detectable group, it is preferred that interactions be detected using automated quantification of the detectable group. For this purpose, it is preferred that the detectable group include a component that produces, either directly or indirectly, a quantifiable signal. Preferred components of this type are radioactive isotopes. Reagents and methods for the use and detection of radioactive labels are well known.

Simultaneous gel shift assays are preferably accomplished by subjecting multiple binding solutions to electrophoresis in a single gel with multiple lanes, and in multiple gels each with multiple lanes. Detection and comparison of multiple samples can be accomplished by, for example automated detection and localization of interacting complexes in the gel lanes.

It is preferred that the test compounds be mixed with either the RNA molecule, either before, during or after formation of the binding solution, or the RNA binding protein prior to addition to the binding solution. For this purpose, it is preferred that the test compound be mixed with either the RNA molecule or the RNA binding protein depending on with which of these components it is desired or expected the test compound will interact. For example, if compounds affecting the interaction of an RNA and an RNA binding protein via interaction with the RNA are desired (or expected, given the nature of the test compounds), then the test compound should be added to the RNA. Conversely, if compounds affecting the interaction of an RNA and an RNA binding protein via interaction with the RNA binding protein are desired (or expected, given the nature of the test compounds), then the test compound should be added to the RNA binding protein. It is most preferred that the test compound be added to the binding solution after heating and cooling and before addition of the RNA binding protein. It is also preferred that all of the test solutions in a given set of test solutions have the test compound mixed in the same way and at the same stage for all of the assays.

3. Identified compounds. Compounds identified as having an effect on interactions between RNA molecules and RNA binding proteins can be used to affect such interactions in cells. In the case where the interaction between an RNA molecule and an RNA binding protein affects the function or expression of the RNA molecule, a compound having an effect on the interaction is expected to have an effect on the function or expression of the RNA molecule. Thus, it is contemplated that compounds identified having an effect on the interaction of an RNA molecule and an RNA binding protein will be useful for affecting the function or expression of the RNA molecule in a cell. Such compounds can be delivered to cells in any manner which allows the compound to have the desired effect. Many such modes of delivery are known in the art. A preferred form of delivery for in vivo applications are compositions combining an identified compound and a pharmaceutically acceptable carrier. For this purpose, the disclosed method can include a step of forming such a composition. For in vitro and ex vivo applications, an identified compound can be added to the culture medium. The compound can also be combined with any delivery system or composition that can enhance the entry of the compound into the cell and/or enhance the delivery of the compound to particular cells.

Suitable pharmaceutical vehicles for administration to a patient are known to those skilled in the art. For parenteral administration, the compound can be dissolved or suspended in sterile water or saline. For enteral administration, the compound can be incorporated into an inert carrier in tablet, liquid, or capsular form. Suitable carriers may be starches or sugars and include lubricants, flavorings, binders, and other materials of the same nature. The compound can also be administered locally at a desired site by topical application of a solution or cream.

Alternatively, the compound may be administered in, on or as part of, liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A good review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214.

The criteria for assessing response to therapeutic modalities employing an identified compound is dictated by the specific condition and will generally follow standard medical practices. Generally, the effect of administration of a compound can be assessed at least by determining if the RNA/RNA binding protein interaction determined to be affected by the compound is in fact affected in cells to which the compound is administered or delivered. Such an assessment can also be made by determining if there is an effect on a surrogate for the interaction, such as expression of an RNA, production of a protein, or a consequent physiological effect. Where the RNA/RNA binding protein interaction affected by the protein is known or suspected to involve the function or expression of an RNA involved in a disease condition, the effectiveness of administration of the compound can be assessed by measuring changes in characteristics of the disease condition.

EXAMPLES

Example 1

Development of optimum universal assay conditions

Universal conditions for the assay to detect interaction between RNA binding proteins and RNA molecules were optimized using gel mobility shift to detect interactions. The assay was performed generally as described above. Specifically, a binding solution was formed by mixing an RNA binding protein sample, an RNA molecule, and buffer components. The buffer components included a buffer, a monovalent cation, a divalent cation, a reducing agent, and a density agent. The type and concentration of the various buffer components were varied to assess their effect on binding and to determine which composition of the buffer components facilitated interactions of RNA binding proteins with a variety of RNA molecules.

RNA Binding Proteins: A protein extract from SH-SY5Y cells was used as the RNA binding protein sample. Protein extracts have also been prepared and tested from numerous other cell lines including HeLa, K562 and primary astrocytes and from tissue samples, for example, rat brain. The SH-SY5Y extract was prepared as follows. A sample of SH-SY5Y cells was divided into 10 large cultures 30 ml each in T150 flasks ($9.9 \times 10^5$ cells/flask). The media was removed, the cells were placed in 150 cc dishes, washed in 1× PBS, and scraped in PBS. The cells were then counted as follows: ($73 \times 10^4$ cells/ml)×(42 ml)×(10 (×dil))=$3.1 \times 10^8$ cells total. After counting, the PBS was removed and 400 μl lysis buffer (per dish) was added. The lysis buffer had the following composition:

| 10 ml | stock concentration | final concentration |
|---|---|---|
| 250 μl | 1 M Tris HCl (pH 7.9) | 25 mM Tris-HCl (pH 7.9) |
| 20 μl | 50 mM EDTA | 0.5 mM EDTA |
| 100 μl | 10 mM PMSF | 0.1 mM phenylmethyl sulfonyl fluoride |
| 100 μl | 200 mM sodium fluoride | 2 mM sodium fluoride |
| 100 μl | 200 mM sodium pyro-phosphate | 2 mM sodium pyro-phosphate |

The cells were then frozen at −20° C. for 30 minutes, thawed, and centrifuged at 15000 g at 4° C. for 15 minutes. The supernatant was divided into 100 μl aliquots and stored at −80° C.

RNA Molecules: AUUUA, amyloid precursor protein (APP) untranslated region (UTR), and poly(A) were used as the RNA molecules in separate assays. These were chosen to assess the ability of the assay to detect interactions using disparate RNA molecules. The RNA molecules were prepared by in vitro transcription by SP6 or T7 RNA polymerase. To facilitate detection of interactions, $^{32}$P-UTP was incorporated into the RNA molecules during transcription. Many in vitro transcription kits are commercially available and optimized for efficient RNA synthesis. The RNA molecules were prepared generally as described by Sambrook et al. and Ausubel et al. Briefly, a reaction mix containing 2 μl 10× transcription buffer (400 mM Tris-HCl, pH 7.5, 60 mM MgCl$_2$, 20 mM spermidine, 50 mM NaCl), 1 μl each of ATP, CTP, and GTP (10 mM), 2 μl 50 μM UTP, 2.5 μl $^{32}$P-UTP, 2 μl linear transcription template (approximately 100 ng) and 2 μl enzyme mix (RNase Inhibitor and 20 U RNA polymerase) was prepared in a final volume of 20 μl. Unless otherwise indicated, all dilutions were made with DEPC treated water. This reaction mixture was incubated for 2 hours at 37° C. Then 1 μl of RNase-free DNase I was added and the reaction incubated for 15 minutes at 37° C. Finally, 20 μl water and 40 μl phenolchloroform were added and the reaction was extracted. The unincorporated nucleotides are then removed by gel filtration through G-25 spin columns.

Optimizing Buffer: The first variable in the assay is the buffer. Tris, HEPES, and Bis-Tris Propane (BTP), were tested for efficiency at promoting interactions with the test RNA molecules. For these assays the buffer was at a concentration of 7.5 mM, the protein concentration was 0.2 μg/μl, and the binding solution included 10 mM KCl, 0.2 mM DTT, 10% glycerol, and 0.2 μg/μl tRNA as competitor for non-specific RNA/protein interactions. Assays were also performed to determine the optimum pH for the buffer. The buffers studied were HEPES at pH 8, Bis-Tris Propane at pH 8 and 7.5, and Tris at pH 8 and pH 7.4. All three buffers allowed for the binding interaction for all three RNA molecules. While there was little difference between them, the use of BTP resulted in significant binding in all cases and, since it has the largest range of buffering capacity, was chosen as the buffer for further optimization.

For all RNA molecules studied, the optimal pH appeared to be 8 or 9. Significant binding was observed for each RNA molecule at pH 10, a condition in which RNase T$_1$ inhibition becomes evident. Conversely low pH seems to inhibit binding. The results are summarized in the table below:

|  | pH | | | | |
| --- | --- | --- | --- | --- | --- |
| RNA | 6 | 7 | 8 | 9 | 10 |
| APP | − | − | + | ++ | ++ |
| AUUUA | − | ++ | ++ | ++ | ++ |
| poly(A) | − | ++ | ++ | ++ | + |

Based on these results, the preferred assay will be composed of RNase $T_1$, tRNA as the non-specific competitor, and a buffer consisting of BTP at pH 8.5.

Optimizing Cations: Another aspect of kit development was the optimization of monovalent and divalent cations. Three monovalent ($K^+$, $Na^+$, and $NH_4^+$) and three different divalent cations ($Mg^{++}$, $Ca^{++}$, and $Fe^{++}$) were analyzed. These were tested at various concentrations (0, 0.1, 1, 10, 50, 100 and 250 mM). The optimal monovalent cation was then tested with the individual divalent cation concentrations and vice versa.

Three monovalent ($K^+$, $Na^+$, and $NH_4^+$) cations were first tested at concentrations ranging from 0 to 500 mM. Initially, 0, 0.2, 2, 12.5, 20, and 50 mM concentrations of each cation were tested for effects on RBP/RNA complex formation for APP, AUUUA, and poly(A). The SH-SY5Y protein extract and a binding buffer consisting of 20 mM Bis-Tris propane at pH 9.0, previously demonstrated to result in optimal binding interactions, were used in addition to the cation and probe. No significant differences were noted for either concentration or cations at 0 to 50 mM. Higher concentrations were then tested.

The studies of divalent cation effects of RBP/RNA interactions were also initiated. The concentration effect of $Mg^{++}$ on the complex formation between APP RNA and proteins (SH-SY5Y) was examined first. The results showed that at lower concentrations ($\leq 10$ mM) of $Mg^{++}$, normal complex formation was observed. At higher concentrations (10 mM, 50 mM, 100 mM, 250 mM) $Mg^{++}$ inhibited the interaction between APP RNA and proteins to differing degrees.

The wide concentration range of monovalent cations capable of promoting interactions compared to the relatively narrow range for divalent is likely due to APP adapting tertiary structures which depend on divalent cations. This would suggest that AUUUA and poly(A) interactions may not be as dependent on divalent cations since they are presumably linear structures.

The concentration effects of divalent cations ($Mg^{++}$, $Ca^{++}$ and $Fe^{++}$) on the complex formation between APP, AUUUA and poly(A) RNA and proteins (SH-SY5Y) were then examined. The results demonstrated that 1 mM for all three divalent cations is the optimal concentration for the detection of interactions between RNAs (APP, AUUUA and poly(A)) and proteins (SH-SY5Y) under the selected binding condition. At higher concentration (10 mM, 50 mM, 100 mM, 250 mM), $Mg^{++}$, $Ca^{++}$ and $Fe^{++}$ inhibited the complex formation to varying degrees. Following a comparison of all three divalent cations at the optimal concentration for binding interactions (1 mM), $Mg^{++}$ was selected for further studies.

The effects of individual monovalent salt concentrations (0, 50, 100, and 500 mM) on AUUUA, APP, and poly(A) RNA's binding to SH-SY5Y protein were also completed. The monovalent cations used were $K^+$, $Na^+$ and $NH_4^+$. RNA-protein complexes form in a much broader monovalent salt concentration (0 to 100 mM) than was observed for the divalent cations (0 to 5 mM) with the optimal monovalent salt concentration being determined to be 50 mM. The binding interaction with the cis-element of APP for all three monovalent cations was compared at 50 mM and KCl was chosen based on its ability to promote the RBP/RNA interaction.

The monovalent ($K^+$) and divalent ($Mg^{++}$) cations were then combined to determine the best concentrations use in the development of the detection kit. Combinations of 10, 50 and 100 mM $K^+$ with 1 mM $Mg^{++}$ and 0.1 mM, 1 mM, and 2.5 mM $Mg^{++}$ with 50 mM $K^+$ were analyzed. The results showed that the combination of 50 mM $K^+$ with 1 mM $Mg^{++}$ is better than the other combinations for detecting APP RNA-protein interactions. This result was confirmed by using AUUUA RNA and poly(A) RNA.

Use of Reducing Agents: The effects of reducing agents were studied by comparing the binding reaction under the previously established conditions (0.2 mM DTT), substituting 0.2 mM β-mercaptoethanol for the DTT, or in the absence of a reducing agent. In five of the six interactions studied, the presence or absence of reducing agent had no effect on the binding interaction. Similarly, no effect of reducing agent was observed with poly(A) RNA and binding protein derived from K562 cells. However, when binding protein was isolated from HeLa cells, a reproducible effect was observed with DTT enhancing the interaction better than β-mercaptoethanol which in turn was better than no reducing agent. The requirement of DTT for certain reactions suggests that its use is preferred as a component of the buffer.

Use of Density Agents: The binding efficiencies of six different RNAs were tested in the presence of 10% glycerol, 10% polyethylene glycol, or no density agent, under buffer, cation and reducing conditions described above. Although no quantitative differences were detected, the addition of glycerol or PEG enhanced the quality of the band on the gel mobility assay. In the absence of a density agent the bands were clearly more diffuse. Thus, while not required, the addition of 10% glycerol is preferred.

Based on this work, the optimal buffer components were determined to be BTP at pH 8.5, 50 mM KCl, 1 mM $MgCl_2$, 0.2 mM DTT and 10% glycerol. These conditions have been used for further validating assays as described below. A BTP concentration of 7.5 mM was used.

Heating Step: The next phase involved screening twelve other RNA elements for detection of interactions under the selected conditions. These assays were also run in the presence of specific and non-specific competitor RNA. The first two cis-elements studied were the Iron Response Element (IRE) and histone RNA. In each case, binding was detected but very inefficiently. Since these had been reported to form secondary structures, we heated the labeled RNA to 80° C. and then cooled the sample to 37° C. after forming the binding solution and before adding the RNA binding proteins. This was intended to break any incorrect structures that may have formed in the RNA and it greatly facilitated the detection of interactions. For both cis-elements specific interactions were detected under our conditions. RNAs of various sizes and structures have been tested under the above conditions and shown to form interactions with binding proteins consistent with those reported in the literature. The binding proteins tested contain various motifs, including RGG boxes, KH domains and Arg-rich proteins.

The preferred method for detecting interactions between RNA molecules and RNA binding proteins involves (1) forming a binding solution including RNA molecules, BTP at pH 8.5, 50 mM KCl, 1 mM $MgCl_2$, 0.2 mM DTT, and 10% glycerol, (2) heating the binding solution to denature the RNA molecules, (3) cooling the binding solution, (4) adding RNA binding proteins to the binding solution, and (5) detecting the interactions between the RNA molecules and the RNA binding proteins.

Example 2

Assays Using Universal Conditions

Several assays were performed demonstrating the usefulness of the universal assay conditions described in Example 1 for detecting interactions between various RNA molecules and RNA binding proteins. In the first assay, interactions of several RNA molecules (radioactively labeled) with different recognition features were incubated with SH-SY5Y or CHL/260 protein extract. The RNA molecules were chosen to highlight detection of interactions dependent on RNA sequence (AUUUA RNA), sequence and RNA structure (histone RNA), or RNA structure alone (double-stranded RNA). In addition to these small RNA molecules (less than 30 nucleotides), the 210 nucleotide 5' untranslated region of glucose transporter type 1 (Glut1) was also tested. The results are shown in FIG. 1. SH-SY5Y protein extract was used with AUUUA RNA and CHL/260 protein extract was used with the remaining RNA molecules. The multiple slower migrating bands in each of the lanes indicate that the universal assay conditions allow detection of interactions between RNA molecules and RNA binding proteins across the spectrum of interaction types.

Figure 2:
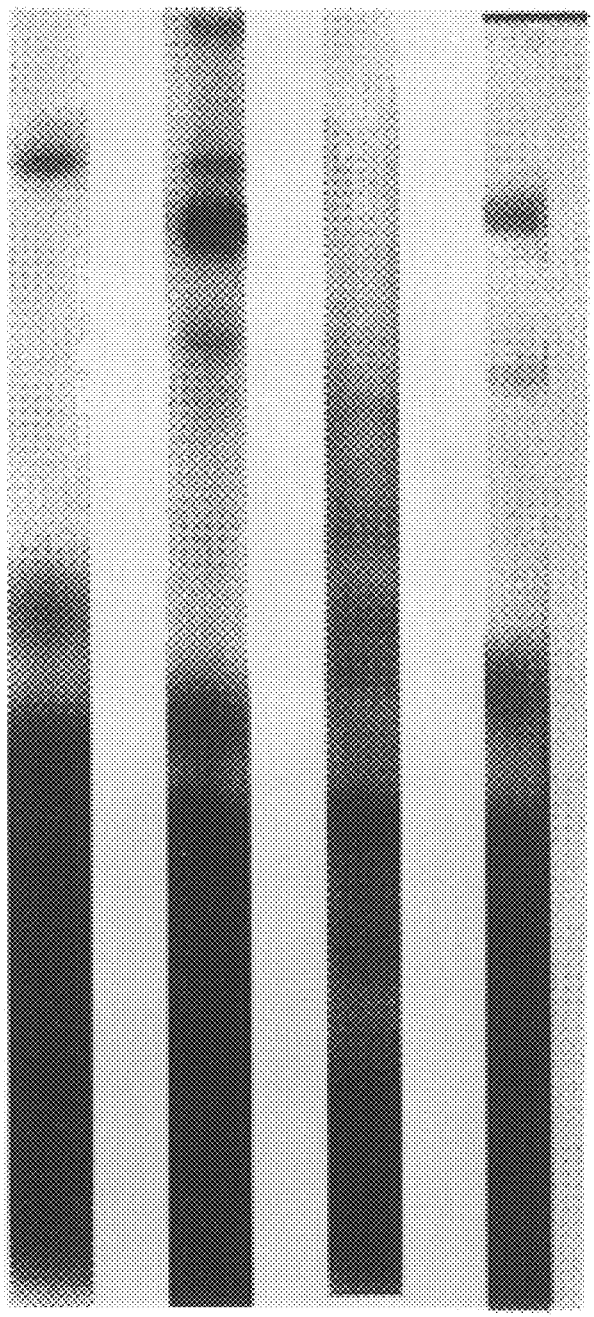
FIG. 2 is a digitized image of a gel mobility shift assay gel showing the relative migration of radioactive RNA molecules. Four different radioactive RNA molecules representing the targets of specific RNA binding protein motifs were incubated with SH-SY5Y or CHL/260 protein extract or recombinant Rev protein and altered mobility of the RNA molecules in a gel is indicated by slow migrating radioactive bands or smears. The RNA molecules represent targets for RNA binding proteins containing double-stranded RNA binding motifs (IRE-BF), RGG box (APP-BF), Arg-rich motifs (RRE-BF), and RNP motifs (U1-BF).

In another assay, interactions of several RNA molecules representing targets for different binding motifs were incubated with SH-SY5Y or CHL/260 protein extract or recombinant Rev protein. The RNA molecules were chosen to highlight detection of interactions involving RNA binding proteins containing double-stranded RNA binding motifs (IRE-BF), RGG box (APP-BF), Arg-rich motifs (RRE-BF), and RNP motifs (U1-BF). The results are shown in FIG. 2. SH-SY5Y protein extract was used in the APP-BF assay, CHL/260 protein extract was used with the IRE-BF and U1-BF assays, and recombinant Rev protein was used with the RRE-BF assay. The multiple slower migrating bands in each of the lanes indicate that the universal assay conditions allow detection of interactions between RNA molecules and RNA binding proteins across the spectrum of interaction types.

Figure 3:
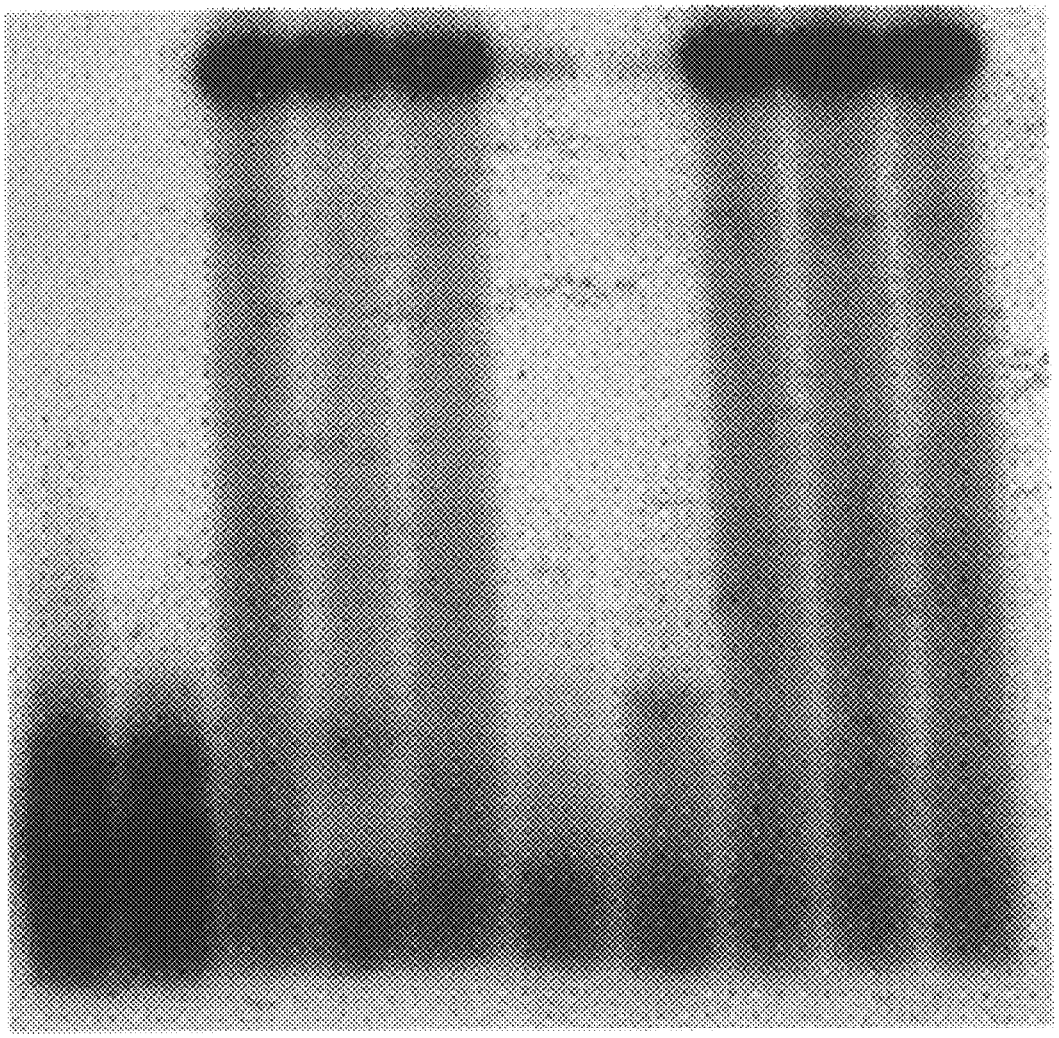
FIG. 3 is a digitized image of a gel mobility shift assay gel showing the relative migration of radioactive RNA molecules. Radioactive RNA molecule IRE was incubated in the presence (lanes 3–10) or absence (lanes 1 and 2) of K562 protein extract and altered mobility of the RNA molecules in a gel is indicated by slow migrating radioactive bands or smears. Assays run in lanes 5–7 were incubated in the presence of increasing concentrations (100×, 1,000×, and 10,000×, respectively) of unlabeled IRE. Assays run in lanes 8–10 were incubated in the presence of similar concentrations of a mutant IRE which is defective for binding.

In another assay, the specificity of the interaction being detected was confirmed. Radioactively labeled IRE RNA was incubated in the presence or absence of K562 protein extract. To test whether interactions detected were specific or not, unlabeled IRE was also included in some of the assays. This RNA competes with the labeled IRE RNA for interaction with RNA binding proteins. As a control, unlabeled mutant IRE (which is defective for binding) was included in some assays. If the interaction is specific, this RNA should not compete with the labeled IRE RNA for the RNA binding proteins. The results of these assays are shown in FIG. 3. Lanes 1 and 2, where no protein extract was included, show no mobility shift, as expected. Lanes 3 and 4, where protein extract was included, show a clear mobility shift. Lanes 5–7 show assays where increasing concentrations (100×, 1,000×, and 10,000×, respectively) of unlabeled IRE RNA was included. This unlabeled RNA effectively competes with the labeled RNA for interaction with the RNA binding proteins as can be seen for the abolition of mobility shift in lanes 6 and 7. Lanes 8–10 show assays where increasing concentrations (100×, 1,000×, and 10,000×, respectively) of mutant IRE RNA was included. This unlabeled RNA is unable to compete with the labeled RNA for interaction with the RNA binding proteins as can be seen from the unchanged mobility shift in lanes 8–10. This clearly shows that the competitive effect of unlabeled IRE RNA seen in lanes 6 and 7 is not due to non-specific interactions between the RNA molecules and the RNA binding proteins.

The universal assay conditions are also beginning to be used in high throughput screening assays for compound isolation. Such assays will analyze combinatorial libraries for compounds capable of altering the binding properties of the RBP to the RNA, with the RNA being targeted. The information obtained from RNA mapping and peptide mapping will be used in molecular modeling to rationally design compounds capable of modulating the interaction of the RNA binding protein with the RNA molecule.

Example 3

Development of High-Throughput Screening Assay

The following assays demonstrate modes and the effectiveness of the disclosed high throughput screening assay. All binding reactions are performed in 96-well polystyrene plates in a final volume of 10 or 100 $\mu$l. The assays were constituted and performed as described below. Specifically, assays were performed by (1) forming a binding solution including RNA molecules, 7.5 mM BTP at pH 8.5, 10 mM KCl, 5 mM $MgCl_2$, 0.2 mM DTT, and 10% glycerol, (2) heating the binding solution to denature the RNA molecules, (3) cooling the binding solution, (4) adding RNA binding proteins to the binding solution, (5) loading the binding solution onto a filter, and (6) detecting the amount RNA retained on the filter. It is preferred that the samples be loaded on to a filter of either pure nitrocellulose or a mixed cellulose ester (MCA). It is also preferred that the filters have a 0.2$\mu$ pore size, although filters with a 0.45$\mu$ pore size will also bind the RNA/RNA binding protein complex. It is preferred that, prior to loading the binding solution onto a filter, the volume is increased. For this purpose, it is preferred that the dilution solution has the same buffer components as the binding solution except lacking the density agent. For a 10 $\mu$l volume it is preferred that the final volume be about 100 $\mu$l by addition of 1× binding buffer. It is also preferred that the binding solution be loaded onto the filter under vacuum. It is also preferred that the filter is washed twice prior to detecting the amount of RNA retained on the filter. Preferably the wash solution had the same composition as the dilution solution. However, TE (pH 8.0), PBS, or TCA can also be used as wash solutions. In most of the assays described below, the RNA molecules were labeled with $^{32}P$.

The nitrocellulose filter plate was precoated with BSA, PVP, polyG, polyI, polyC, polyU or tRNA as blocking agents prior to loading the assay solutions. Regardless of whether the well was untreated ore precoated with a blocking agent, the free RNA cpms (that is, RNA retained on the filter in the absence of RNA binding protein) were 7 to 12% of the protein-bound cpms. This indicates that blocking is not required or preferred.

Optimizing Protein Concentration

Results from gel mobility shifts demonstrate that not all the RNA added to the reaction is shifted by 2 $\mu$g of protein extract, thus protein titrations were carried out to maximize the number of counts detected so that there will be a greater difference range for detection of active compounds. This was also expected to increase the ratio of bound:free RNA. The amount of protein extract (SH-SY5Y or K562, depending on which RNA was used) was titrated from 1 to 10 μg protein/reaction in increments of 1 μg. The results were, for all RNA/protein combinations tested (APP/SH-SY5Y; IRE/K562; AUUUA/K562; nAChR/SH-SY5Y; His/K562, U1/K562; Glut-1/K562), a concentration-dependent rise in protein-bound cpm's up to roughly 5 to 7 μg, where the reaction reached a plateau and decreased slightly through 10 μg. Taken together, these results indicate that the optimal concentration of protein extract is greater than about 0.5 μg/μl. The data is summarized in Table 1. It was found in most cases that the half maximal concentration for wild-type binding was in the 2 to 4 μg range. It is preferred that the amount of protein extract used in the screen be in to 2 to 4 μg range to facilitate detection of compounds that both enhance or inhibit the RNA/RNA binding protein interaction. When labeled mutant RNAs were tested they also produced detectable counts, but the absolute number of cpms bound are 5 to 100 times lower than for wild-type RNAs.

TABLE 1

| Probe | Plateau | Half maximal conc. |
|---|---|---|
| His-WT | 7 μg (n = 14, 7 w/T1, 7 w/o T1) | 3.7 μg (w/ or w/o T1) |
| His-MUT | 4.8 μg (n = 3) | 2.7 μg |
| AUUUA | 8 μg (n = 2, w/ or w/o T1) | 4 μg (w/o T1), 2.25 μg (w/T1) |
| U1-WT | 5 μg (n = 8) | 2 μg |
| U1-MUT | 7 μg (n = 4) | 2 μg |
| Glut-1 | 8.25 μg (n = 2) | 2.4 μg (w/o T1), 3 μg (w/T1) |
| IRE-WT | 5 μg (n = 6) | 1.5 μg |
| IRE-MUT | 5 μg (n = 4) | 3 μg |
| APP | 5 μg (n = 1) | 2 μg |

Competition Assays

Figure 4:
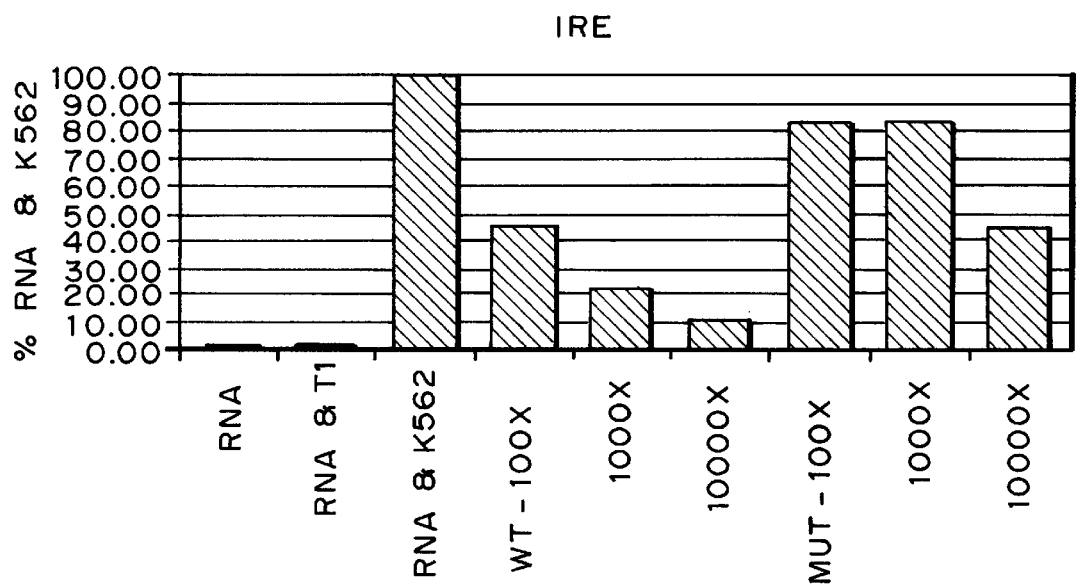
FIG. 4 is a graph of the amount of radioactively labeled RNA (expressed in percent of the amount of RNA retained on a filter in a reference binding solution) retained on a filter following loading of various binding solutions. All of the binding solutions contained radioactively labeled IRE RNA either alone or including various other components. The first two lanes represent binding solutions without RNA binding protein. RNA & T1 indicates that the binding solution was treated with RNase T1 prior to loading the filter. The remaining columns represent binding solutions containing RNA binding protein (K562 extract). WT indicates that the binding solution included the indicated amount of unlabeled wild type RNA as a competitor. MUT indicates that the binding solution included the indicated amount of unlabeled mutant RNA as a competitor.

To test the ability of the filter assay to detect changes in binding activity (that is, decreased interaction between RNA and RNA binding proteins) competition assays were performed with IRE RNA and K562 protein extract (see FIG. 4). Competition experiments were performed by adding increasing concentrations (100 to 10,000×) of unlabeled wild-type or mutant IRE RNA to the binding reaction. FIG. 4 illustrates the results. A concentration dependent inhibition of binding was observed in assays in which the unlabeled wild-type RNA was added whereas no competition was observed in assays in which unlabeled mutant RNA was added.

Figure 5:
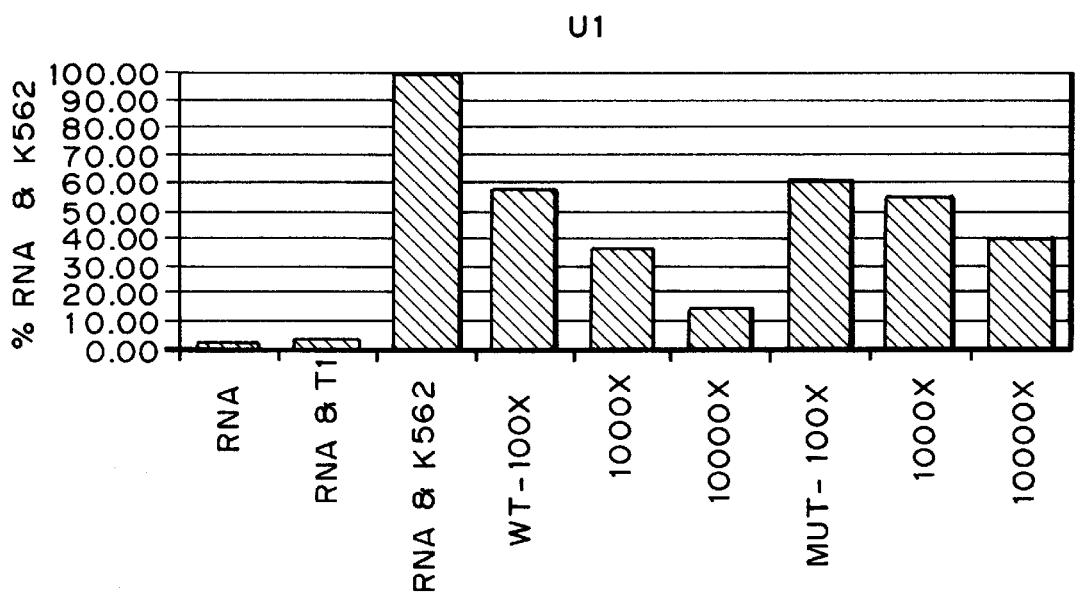
FIG. 5 is a graph of the amount of radioactively labeled RNA retained on a filter (expressed in percent of the amount of RNA retained on a filter in a reference binding solution) following loading of various binding solutions. All of the binding solutions contained radioactively labeled U1 RNA either alone or including various other components. The first two columns represent binding solutions without RNA binding protein. The remaining columns represent binding solution containing RNA binding protein (K562 extract). WT indicates that the binding solution included the indicated amount of unlabeled wild type RNA as a competitor. MUT indicates that the binding solution included the indicated amount of unlabeled mutant RNA as a competitor.

To more fully test the filter assay, competitions were performed with U1 and His RNA's as well. Both U1 and His wild-type RNA's showed a concentration dependent inhibition of binding (see FIG. 5). However, the mutant RNA's also inhibited binding in a concentration dependent manner, although at about a 10-fold higher concentration. FIG. 5 illustrates these results for the U1 competition. In these competition assays, unlike the IRE assay, the mutant RNA used has been shown to bind the RNA binding protein, although with a lower affinity than the wild-type RNA. The results of the U1 and His filter assay competitions reflect the ability of the assay to detect low affinity as well as higher affinity binding interactions.

Modulation of the Binding Interaction by Small Molecules

Figure 6:
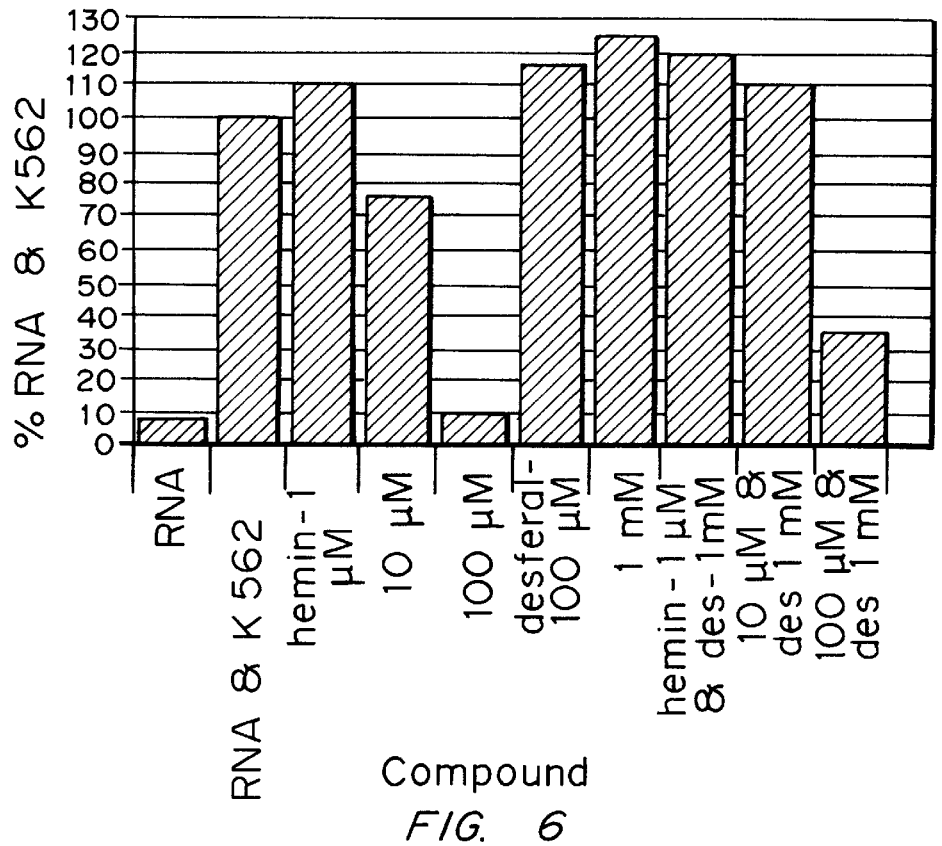
FIG. 6 is a graph of the amount of radioactively labeled RNA retained on a filter (expressed in percent of the amount of RNA retained on a filter in a reference binding solution) following loading of various binding solutions. All of the binding solutions contained radioactively labeled IRE RNA either alone or including various other components. The first column represents a binding solution without RNA binding protein. The remaining columns represent binding solutions containing RNA binding protein (K562 extract). Hemin indicates that the binding solution included the indicated amount of hemin as a test compound. Desferal and des indicate that the binding solutions included the indicated amount of desferroxiamine as a test compound.

Binding assays were performed with wild-type IRE RNA and K562 protein extract in the presence of sources of iron or iron chelators to determine the ability of the filter assay to detect the modulation of binding interactions by small molecules. Increasing concentrations the iron sources hemin (1 to 100 μM) and $FeCl_3$ (1 μM to 1 mM) or the iron chelator desferroxiamine (1 μM to 1 mM) were added to the binding reactions (see FIG. 6). Hemin and $FeCl_3$ produced a concentration-dependent inhibition of binding. Desferroxiamine did not change the amount IRE/protein complex formed, perhaps because there is not enough iron in the cell extract to produce a noticeable change upon addition of desferroxiamine. The reactions were analyzed by gel shifts to visualize the results of the filter assay.

Exploratory Library Screen

A 96 member exploratory compound library that contained CNI-1493, a compound previously shown to post-transcriptionally inhibit TNF-α production, was generated. The library was initially screened at 10 μM against $^{32}$P-labeled AUUUA RNA. Several methods of introducing the compounds into the binding reaction were tested. Initially the compounds were coincubated with the RNA and protein, producing modest results. Next, preincubation with either the protein extract or the RNA was tried with improved results.

Figure 7:
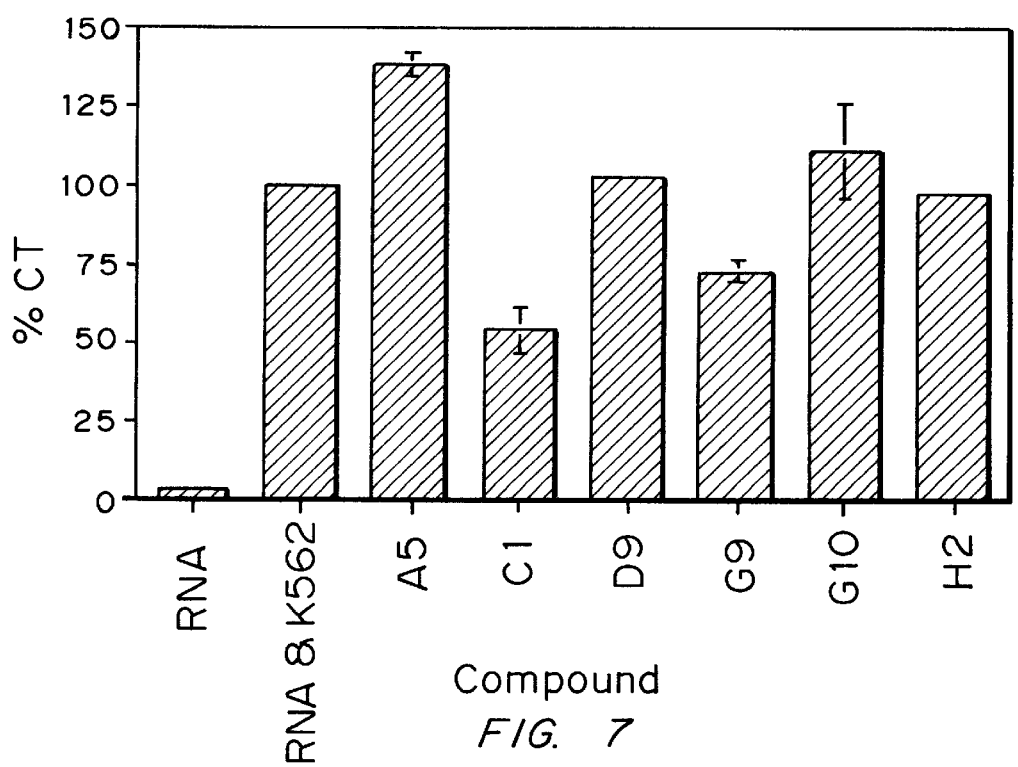
FIG. 7 is a graph of the amount of radioactively labeled RNA retained on a filter (expressed in percent of the amount of RNA retained on a filter in a reference binding solution) following loading of various binding solutions. All of the binding solutions contained radioactively labeled AUUUA RNA either alone or including various other components. The first column represents a binding solution without RNA binding protein. The remaining columns represent binding solution containing RNA binding protein (K562 extract). Columns 3 through 8 correspond to binding solutions including the indicated test compound.

Seventeen compounds were chosen for further analysis at 100 nM, 1 μM and 10 μM using both AUUUA and IRE RNAs based on the results from four screening efforts (Exps. 29–31, 33). Table 2 summarizes the results from these compounds at 10 μM. The results are also shown graphically in FIG. 7. Compound C1 was consistently the most active inhibitor resulting in close to a 50% reduction in counts (p=0.001) while A5 was the most active enhancer increasing counts by 38% over controls (p<0.001). Compound G10, CNI-1493, produced a substantial increase in counts in 3 of the 4 experiments. Compounds D9 and H2, chosen as negative controls from the initial screening, continued to have no effect in the dose dependent screen (Exp. 33) and were identified as vehicle controls. When the 17 compounds were screened against IRE RNA, a differential effect was seen with compound A5 (see FIG. 8). This most efficacious enhancer of AUUUA binding failed to have an effect on IRE.

TABLE 2

| | Experiment # | | | | | | |
|---|---|---|---|---|---|---|---|
| Compound | #33 | #31 | #30 | #29 | Compound | Avg. % | SEM |
| RNA | 1.84 | 2.57 | 1.98 | 1.48 | RNA | 1.97 | 0.28 |
| RNA & K562 | 100.00 | 100.00 | 100.00 | 100.00 | RNA & K562 | 100.00 | |
| A3-10 μM | 103.79 | 67.58 | 92.35 | 82.69 | A3-10 μM | 86.60 | 7.69 |
| A4-10 μM | 104.74 | 93.36 | 62.58 | 98.27 | A4-10 μM | 89.74 | 9.35 |
| A5-10 μm | 144.10 | 145.00 | 133.15 | 130.31 | A5-10 μm | 138.14 | 3.75 |
| A11-10 μm | 101.75 | 96.59 | 76.95 | 82.91 | A11-10 μm | 89.55 | 5.78 |
| C1-10 μm | 64.52 | 39.48 | 43.08 | 68.93 | C1-10 μm | 54.00 | 7.44 |

TABLE 2-continued

| Compound | Experiment # #33 | #31 | #30 | #29 | Compound | Avg. % | SEM |
|---|---|---|---|---|---|---|---|
| C8-10 µm | 104.98 | 79.45 | 85.32 | 79.37 | C8-10 µm | 86.53 | 6.42 |
| D9-10 µm | 105.10 | 105.54 | 100.69 | 99.68 | D9-10 µm | 102.75 | 1.50 |
| E7-10 µm | 99.20 | 87.16 | 74.40 | 93.46 | E7-10 µm | 88.55 | 5.32 |
| F6-10 µm | 100.10 | 82.17 | 57.89 | 85.68 | F6-10 µm | 81.46 | 8.76 |
| G1-10 µm | 89.62 | 80.62 | 94.23 | 80.16 | G1-10 µm | 86.16 | 3.46 |
| G6-10 µm | 91.49 | 85.57 | 92.72 | 80.41 | G6-10 µm | 87.55 | 2.85 |
| G7-10 µm | 94.62 | 82.06 | 62.38 | 79.87 | G7-10 µm | 79.73 | 6.63 |
| G9-10 µm | 68.52 | 81.48 | 74.65 | 67.25 | G9-10 µm | 72.98 | 3.26 |
| G10-10 µm | 135.24 | 127.28 | 66.94 | 114.53 | G10-10 µm | 111.00 | 15.29 |
| G11-10 µm | 93.50 | 87.91 | 88.39 | 85.17 | G11-10 µm | 88.74 | 1.74 |
| G12-10 µm | 93.56 | 86.39 | 86.37 | 84.10 | G12-10 µm | 87.60 | 2.06 |
| H2-10 µm | 93.39 | 97.31 | 103.77 | 95.65 | H2-10 µm | 97.58 | 2.20 |

Analysis

Competition studies have been performed using the filter assay in which unlabeled wild-type or mutant RNA is added to the reaction at 100 to 10,000 times the concentration of $^{32}$P-RNA to compete for the protein binding of the radiolabeled RNA. It has been demonstrated the high-throughput assay can be used effectively for this type of study using a variety of RNA molecules including IRE, AUUUA, APP, U1, and His. Using IRE, a concentration dependent inhibition of binding by unlabeled wild-type RNA has been shown, with no effect shown by unlabeled mutant RNA, except at the highest concentration. These results have been confirmed by gel shift analysis. Furthermore, the disclosed assay can be used to detect more subtle differences in the ability of various RNA molecules to bind protein as demonstrated by the results of the U1 and His experiments. In this case, the mutant RNA has a weak binding affinity for the RNA binding protein. When unlabeled mutant RNA is added to the binding reaction, a slight concentration dependent inhibition is detected with maximum inhibition of 50 to 70% occurring at 10,000 times the $^{32}$P-RNA concentration. In this way, the binding affinity of various altered forms of the binding site of an RNA binding protein can be compared.

A 96 member random compound library was screened with the disclosed high throughput assay. The compounds were initially screened at 10 µM against $^{32}$P-labeled AUUUA RNA. One compound was found to produce a significant increase in detectable counts while two compounds were found to produce a significant decrease in counts. Seventeen compounds were chosen for further analysis at 100 nM, 1 µM and 10 µM using both AUUUA and IRE RNA molecules to determine if any selectivity of the compounds could be detected. When the 17 compounds were screened against IRE RNA, a differential effect was seen with the enhancing compound. The most efficacious enhancer of AUUUA binding failed to have an effect on IRE. Gel shifts of these compounds using AUUUA RNA confirmed the activity of the inhibitors.

Example 4

Figure 9A:
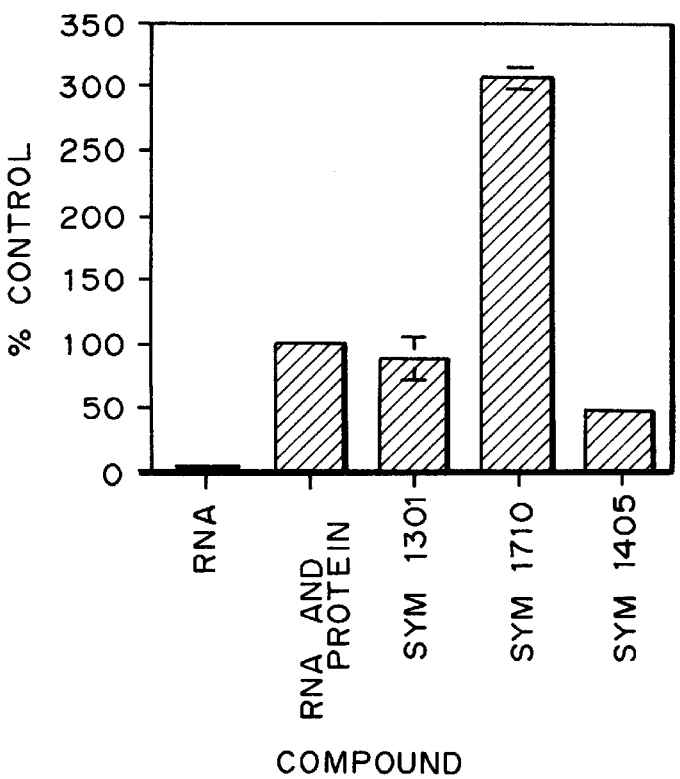
FIG. 9A is a graph of the level of RNA/RBP interactions (between the TNF-α 3' untranslated region and human cell RBP's) in the presence or absence of test compounds. The interaction of radiolabeled TNF-α RNA with human cell extracts was detected in a high throughput screening assay as described in Example 4. The first column shows RNA alone. The second column shows RNA plus extract. The remaining columns include RNA plus extract in the presence of specific compounds.
Figure 9B:
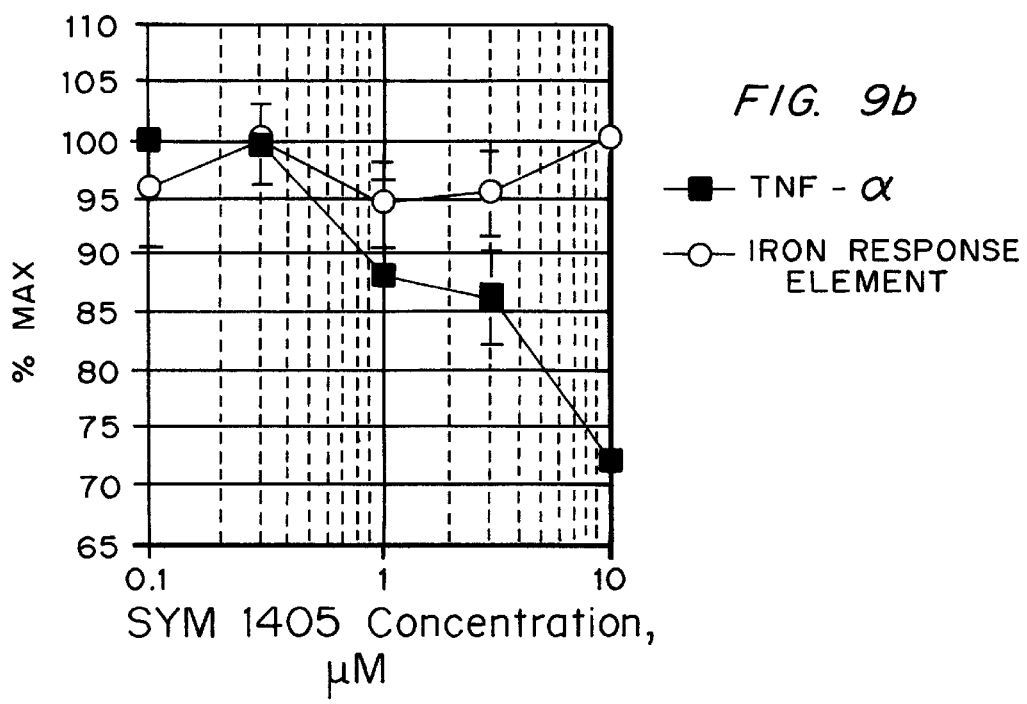
FIG. 9B is a graph of concentration-dependent inhibition of TNF-α RNA/RBP interaction by compound SYM 1405. A control assay using the iron response element shows that the effect is specific for TNF-α.

Screening For Compounds That Modulate Interaction Of RNA Molecules And RNA Binding Proteins This example describes identification of compounds which either increase or decrease the binding interaction between a site within an RNA molecule which interacts with an RBP. This example makes use of a total protein extract which allows identification of compounds that modulate interactions without the need for identification of the specific RBP(s) involved. The 3' untranslated region (UTR) from TNF-α was used in the screening assay described in Example 3 using a combinatorial library of compounds chosen to represent many properties thought to be involved in RNA binding. A number of compounds were identified from the combinatorial library. As shown in FIG. 9A, SYM 1301 had no effect on this interaction, SYM 1710 potentiated binding by approximately 3 fold while SYM 1405 inhibited binding by about 40%. It was determined that SYM 1710 has an $EC_{50}$ of 23 µM and SYM 1405 has an $EC_{50}$ of about 2 µM on in vitro binding. These compounds can now be used to construct focused libraries based on the structures of these compounds. Such focused libraries can then be screened using the disclosed assay to identify compounds that are more effective or more specific. The specificity of SYM 1405 was demonstrated when increasing concentrations of the compound were tested in the assay with TNF-α and an unrelated RNA, the iron response element. FIG. 9B shows that SYM 1405 inhibited binding of TNF-α in a concentration-dependent manner while having little effect on the iron response element.

Those skilled in the art will recognize, or be able to ascertain using no more than routine experimentation, many equivalents to the specific embodiments of the invention described herein. Such equivalents are intended to be encompassed by the following claims. The references cited herein are hereby incorporated by reference.

We claim:

1. A method for identifying compounds that modulate the interactions between RNA binding proteins and RNA molecules, wherein the method is performed under conditions that permit detection of interactions between RNA binding proteins and each of amyloid precursor protein untranslated region, AUUUA, and poly(A), said method comprising:

(a) forming one or more sets of test solutions, each of said test solutions comprising
  (i) one or more different RNA molecules;
  (ii) a buffer, said buffer comprising a monovalent cation, a divalent cation, a reducing agent, and a density agent for enhancing gel band quality;
  (iii) one or more different RNA binding proteins; and,
  (iv) a test compound;
wherein the RNA molecules, buffer, and RNA binding proteins are the same in each test solution within a set, and wherein either the RNA molecules, or RNA binding proteins, or both RNA molecules and RNA binding proteins, differ between the sets of different test solutions;

(b) forming a control solution for each set of test solutions in step (a), each of said control solutions comprising the RNA molecules, buffer, and RNA binding proteins present in each corresponding set of testing solutions in step (a);

(c) detecting the interactions between said RNA binding proteins and RNA molecules in the test solutions and control solutions; and (d) identifying a compound as modulating interactions between the RNA molecules and the RNA binding proteins if the interactions detected in the control solutions and in the test solutions differ.

2. The method of claim 1, wherein forming said test solutions in (a) comprises:

(a) forming said one or more sets of said test solutions by
(i) forming a solution of said RNA molecules and said buffer;
(ii) heating said solution for time and temperature sufficient to denature the RNA molecules;
(iii) cooling said solution;
(iv) adding one or more different RNA binding proteins to said solution; and
(v) adding a test compound to the solution of (i), (ii), (iii), or (iv); and wherein forming said control solutions in (b) comprises set of test solutions in step (a), each performing the steps (i–iv).

3. The method of claim 1, wherein a plurality of sets of test solutions are assayed.

4. The method of claim 1, wherein said buffer is (1) selected from the group consisting of HEPES, Tris, and Bis-Tris Propane, and (2) at a pH between about 8 and 10, wherein said monovalent cation is selected from the group consisting of $K^+$, $Na^+$, and $NH4^+$, wherein said divalent cation is selected from the group consisting of $Mg^{++}$, $Ca^{++}$, and $Fe^{++}$, wherein said reducing agent is selected from the group consisting of dithiothreitol and β-mercaptoethanol, and wherein said density agent is selected from the group consisting of glycerol and polyethylene glycol.

5. The method of claim 4 wherein the buffer is (1) selected from the group consisting of HEPES, Tris, and Bis-Tris Propane, (2) at a pH between about 8 and about 10, and (3) at a concentration of between about 5 and about 100 mM, wherein the monovalent cation is $K^+$ at a concentration of about 50 mM, wherein the divalent cation is $Mg^{++}$ at a concentration of about 1 mM, wherein the reducing agent is dithiothreitol at a concentration of about 0.2 mM, and wherein the density agent is glycerol at a concentration of about 10 percent (v/v).

6. The method of claim 4 wherein the buffer is Bis-Tris Propane at a pH of about 8.5 and at a concentration of about 7.5 mM, wherein the monovalent cation is (1) selected from the group consisting of $K^+$, $Na^+$, and $NH_4^+$, and (2) at a concentration of between 0 and about 100 mM, wherein the divalent cation is $Mg^{++}$ at a concentration of about 1 mM, wherein the reducing agent is dithiothreitol at a concentration of about 0.2 mM, and wherein the density agent is glycerol at a concentration of about 10 percent (v/v).

7. The method of claim 4 wherein the buffer is Bis-Tris Propane at a pH of about 8.5 and at a concentration of about 7.5 mM, wherein the monovalent cation is $K^+$ at a concentration of about 50 mM, wherein the divalent cation is (1) selected from the group consisting of $Mg^{++}$, $Ca^{++}$, and $Fe^{++}$, and (2) at a concentration of between 0 and about 5 mM, wherein the reducing agent is dithiothreitol at a concentration of about 0.2 mM, and wherein the density agent is glycerol at a concentration of about 10 percent (v/v).

8. The method of claim 4 wherein the buffer is Bis-Tris Propane at a pH of about 8.5 and at a concentration of about 7.5 mM, wherein the monovalent cation is $K^+$ at a concentration of about 50 mM, wherein the divalent cation is $Mg^{++}$ at a concentration of about 1 mM, wherein the reducing agent is (1) selected from the group consisting of dithiothreitol and β-mercaptoethanol, and (2) at a concentration of between 0 and about 1 mM, and wherein the density agent is glycerol at a concentration of about 10 percent (v/v).

9. The method of claim 4 wherein the buffer is Bis-Tris Propane at a pH of about 8.5 and at a concentration of about 7.5 mM, wherein the monovalent cation is $K^+$ at a concentration of about 50 mM, wherein the divalent cation is $Mg^{++}$ at a concentration of about 1 mM, wherein the reducing agent is dithiothreitol at a concentration of about 0.2 mM, and wherein the density agent is (1) selected from the group consisting of glycerol and polyethylene glycol, and (2) at a concentration of between about 1 and about 20 percent (v/v).

10. The method of claim 5 wherein the buffer is Bis-Tris Propane at a pH of about 8.5 and at a concentration of about 7.5 mM, wherein the monovalent cation is $K^+$ at a concentration of about 50 mM, wherein the divalent cation is $Mg^{++}$ at a concentration of about 1 mM, wherein the reducing agent is dithiothreitol at a concentration of about 0.2 mM, and wherein the density agent is glycerol at a concentration of about 10 percent (v/v).

11. The method of claim 1, wherein at least one of the RNA binding proteins or at least one of the RNA molecules is labeled with a detectable group, and wherein detecting interactions between the one or more RNA binding proteins and the one or more RNA molecules comprises the steps of (1) separating complexes of interacting RNA binding proteins and RNA molecules from RNA binding proteins and RNA molecules not involved in an interaction, and (2) measuring the labeled RNA binding proteins or labeled RNA molecules involved in said interactions.

12. The method of claim 11 wherein separating complexes of interacting RNA binding proteins and RNA molecules from RNA binding proteins and RNA molecules not involved in an interaction is accomplished by gel electrophoresis or filter binding.

13. The method of claim 12 wherein separating complexes of interacting RNA binding proteins and RNA molecules from RNA binding proteins and RNA molecules not involved in an interaction is accomplished by filter binding, wherein the set of one or more test solutions and the control solution are subjected to filter binding simultaneously in a single apparatus.

14. The method of claim 12 separating complexes of interacting RNA binding proteins and RNA molecules from RNA binding proteins and RNA molecules not involved in an interaction is accomplished by filter binding, wherein a plurality of the one or more test solutions and the control solution are subjected to filter binding simultaneously in a single apparatus.

15. The method of claim 1, said method further comprising analyzing the RNA molecules or RNA binding proteins involved in said interactions.

16. The method of claim 13 further comprising analyzing the RNA molecules or RNA binding proteins involved in interactions.

17. The method of claim 1, said method further comprising comparing the interaction of the one or more RNA binding proteins and the one or more RNA molecules in the presence and absence of one or more competing RNA molecules.

18. The method of claim 1, wherein one RNA binding protein is added to each of the test solutions and the control solution.

19. The method of claim 1, wherein each of the test solutions and the control solution contain one RNA molecule.

20. The method of claim 1, wherein at least one of the one or more RNA molecules is encoded by a gene of interest.

21. The method of claim 20, said method further comprising determining if said compounds identified as modulating said interactions between RNA binding proteins and one or more RNA molecules encoded by said gene of interest also modulate said interactions in a cell, the method comprising the steps of (a) administering said identified compound to a cell in vitro expressing said gene of interest;

(b) measuring expression of said gene of interest; and (c) determining said identified compound modifies said interactions in a cell if said expression in the presence of said compound differs from said expression in a cell without said compound.

22. The method of claim 20 further comprising forming a composition for affecting expression of the gene of interest comprising mixing at least one test compound identified as having an effect on interactions between the RNA molecules and the RNA binding proteins with a pharmaceutically acceptable carrier.

* * * * *

UNITED STATES PATENT AND TRADEMARK OFFICE
CERTIFICATE OF CORRECTION

PATENT NO. : 6,004,749
DATED : December 21, 1999
INVENTOR(S) : Giordano et al.

It is certified that error appears in the above-identified patent and that said Letters Patent is hereby corrected as shown below:

Column 1,
Line 34, after "have" delete -- yet --;

Column 4,
Line 22, replace "represents" with -- represent --;

Column 10,
Line 37, replace "unto" with -- onto --;

Column 11,
Line 15, replace "the" with -- then --;

Column 16,
Line 47, after "identified" insert -- as --;

Column 22,
Line 32, after "amount" insert -- of --;
Line 34, replace "on to" with -- onto --;

Column 25,
Line 24, after "demonstrated" insert -- that --;

Column 27,
Line 13, replace "wherein" with -- wherein: (a) --; and
Line 16, delete "(a) forming said one or more sets of said test solutions by".

Signed and Sealed this

Twenty-eighth Day of May, 2002

Attest:

JAMES E. ROGAN
*Attesting Officer*   *Director of the United States Patent and Trademark Office*